United States Patent [19]

Bowcock et al.

[11] Patent Number: 5,811,233
[45] Date of Patent: Sep. 22, 1998

[54] COMPOSITIONS AND USES THEREOF IN THE DIAGNOSIS OF PSORIASIS

[75] Inventors: Anne Bowcock, Dallas; James Tomfohrde, Arlington; Alan Menter; Richard Gaynor, both of Dallas, all of Tex.

[73] Assignee: Board of Regents, Univ. of Texas System, Austin, Tex.

[21] Appl. No.: 246,855

[22] Filed: May 20, 1994

[51] Int. Cl.[6] .............................. C12Q 1/68; C07H 21/04
[52] U.S. Cl. .......................... 435/6; 536/23.1; 536/24.3; 536/24.31
[58] Field of Search .............................. 435/6; 536/23.1, 536/24.31, 24.3

[56] References Cited

U.S. PATENT DOCUMENTS

| | | | |
|---|---|---|---|
| 4,554,101 | 11/1985 | Hopp ................................. | 260/112.5 R |
| 4,603,102 | 7/1986 | Himmelmann et al. ................. | 430/523 |
| 4,666,828 | 5/1987 | Gusella ........................................ | 435/6 |
| 4,963,663 | 10/1990 | White et al. .......................... | 536/24.31 |

OTHER PUBLICATIONS

Akihiko et al., "Specific Nucleotide Sequence of HLA–C is Strongly Associated with *Psoriasis Vulgaris,*" *Chemical Abstracts*, 118(13) :178, Mar. 1993.
Bowcock, "Genetic Locus for Psoriasis Identified," *Annals of Medicine*, 27(2) :183, 1995.
Botstein, et al., "Construction of a Genetic linkage Map in Man Using Restriction Fragment Length Polymorphisms," *Am. J. Hum. Genet.*, 32:314–331, 1980.
Elder et al., "The Genetics of Psoriasis," *Arch. Dermatol.*, 130:216–224, Feb. 1994.
Lin et al., "Genetic Linkage Studies in Psoriasis," *J. Investigative Dermatology*, 96 (4):535, Apr. 1991.
Kai et al., "Association Between HLA Antigens and Families with *Psoriasis Vulgaris,*" *Chinese Medical Journal*, 106 (2) :132–135, 1993.
Karvonen et al., "HLA Antigens in Psoriasis. A Family Study," *Annals of Clinical Research*, 8:298–304, 1976.
Nair et al., "Exclusion of Tight Linkage Between Familial Psoriasis and HLA Genes Under Single Gene, Autosomal Dominant Model," *J. Investigative Dermatology*, 100 (4) :539, Apr. 1993.
Rosbotham et al., "An Association Between Psoriasis and Hereditary Multiple Exostoses. A Clue for the Mapping of a Psoriasis Susceptibility Gene?" *British Journal of Dermatology*, 130:671–674, 1994.
Swanbeck et al., "A Population Genetic Study of Psoriasis," *Britich Journal of Dermatology*, 131:32–39, 1994.
Search Report, PCT/US95/06356 filed 19 May 1995.
Baadsgaard et al., *Proc. Nat'l. Acad. Sci. USA*, 87:4256–4260, 1990.
Baker et al., *J. Dermatol.*, 126:493, 1993.
Barker, *Lancet*, 338:227, 1991.
Bowcock et al., *Genomics*, 15:376, 1993.
Buckler et al., *Proc. Natl. Acad. Sci. USA*, 88:4005–4009, 1991.
Chumakov et al., *Nature*, 359:380–387, 1992.
Church et al., *Nature Genet.*, 6:98–105.

Duvic, *J. Invest. Dermatol.*, 95:385, 1990.
Hall et al., *Science*, 250:1684, 1990.
Li et al., *Proc. Natl. Acad. Sci. USA*, 88:7739–7743, 1991.
Li et al., *Genomics*, 13:665, 1992.
Lovett et al., *Proc. Natl. Acad. Sci. USA*, 88:9628, 1991.
Matise et al., *Nature Genet.*, 6:384, 1994.
Menter and Barker, *Lancet*, 338:231, 1991.
Morgan et al., *Nucleic Acids Res.*, 20:5173–5179, 1992.
Parimoo et al., *Proc. Natl. Acad. Sci. U.S.A.*, 88:9623, 1991.
Speilman et al., *Am. J. Hum. Genet.*, 52:506, 1993.
Tiilikainen et al., *Br. J. Dermatol.*, 192:179, 1980.
Tomfohrde et al., Abstract, Meeting on Genome Mapping & Sequencing, May 1115, 1994, Cold Spring Harbor, New York.
Tomfohrde et al., *Science*, 264;1141–1145, 1994.
Weeks and Lange, *Am. J. Hum. Genet.*, 50:859, 1992.
Weissenbach et al., *Nature*, 859:794, 1992.
Mukaida et al. (1989) "Genomic Structure of the Human Monocyte–derived Neutrophil Chemotactic Factor IL–8." J. Immunol. 143:1366–1371.
Ujemura et al (1993) "The Cytokine Network in Lesional & Lesion Free Psoriatic Skin . . . " J. Invest. Dermatol. 101:701–705.
Yoshida et al (1993) "DNA Typing of HLA–B Gene in Takayasu's Arteritis." Tissue Antigens 42(2): 87–90.
Cianetti et al. (1989) Three New Class I HLA Alleles: Structure of mRNAs and Alternative Mech. of Processing. Immunogenetics 29: 80–91.
Geraghty, et al (1987) A Major Histocompatibility Complex Class I Gene that Encodes a Protein with Shortened Cytoplasmic Segment. Proc. Natl Acad. Sci. (USA) 84: 9145–9149.

*Primary Examiner*—Jasemine C. Chambers
*Assistant Examiner*—Scott D. Priebe
*Attorney, Agent, or Firm*—Arnold, White & Durkee

[57] ABSTRACT

A psoriasis susceptibility locus defined as among linked members within a family has been identified. The locus is linked to an intron of the interleukin enhancer binding factor gene in some families, while being linked to an interleukin 8 gene in other families demonstrating a familial linked form of psoriasis. The locus identified may be further defined as being located distal to genetic maker D17S784 of human chromosome 17q. This locus does not demonstrate linkage with DNA markers within flanking the HLA cluster of genes. A psoriasis susceptibility locus has also been observed close to the centromere of human chromosome 4. Both identified regions provide positive LOD scores with markers on chromosomes 17q and particularly 2 regions close to the ILF gene or the interleukin 8 gene. Methods of screening a family for psoriasis susceptibility using a defined familial psoriasis susceptibility locus are also disclosed. A cDNA capable of detecting a genetic polymorphism identifying the psoriasis susceptibility locus in families with a psoriasis afflicted member, and a process for preparing such a cDNA, are further disclosed. The molecular probes disclosed herein are also known to hybridize with the distal region of human chromosome 17q and with chromosome 4q, and therefore are useful for detecting a genetic lesion in chromosome 17q and 4q. A psoriasis gene related to familial forms of psoriasis is also disclosed. This gene maps to the distal end of human chromosome 17q and has close proximity or is within a gene encoding interleukin enhancer binding factor.

32 Claims, 8 Drawing Sheets

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:1:

GCGACGCCGC GAGTCCGATA GG                      22

( 2 ) INFORMATION FOR SEQ ID NO:2:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:2:

CCCCACTGCC CCTGGTACCC GCGCGCT                 27

( 2 ) INFORMATION FOR SEQ ID NO:3:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:3:

CTCCAGTGGA TGTATGGCT                          19

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:4:

CCAGCGAACA CGTACACTGT                         20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
CTCGCCGTCT  TCTGTCTTGA                                                          20
```

( 2 ) INFORMATION FOR SEQ ID NO:6:

( i ) SEQUENCE CHARACTERISTICS:
        ( A ) LENGTH: 447 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
CCAGCGAACA  CGTACACTGT  CTCTGGACAA  GCTGTGGTCA  CCCCGGCAGC  CGTGCTGGCC          60
CCTCCTAAGG  CAGAGGCCCA  GGAGAATGGA  GACCACAGGG  AAGTCAAAGT  GAAAGTAGAG         120
CCTATTCCCG  CCATTGGCCA  CGCCACGCTC  GGCACTGCCA  GCCGGATCAT  TCAGACGGCA         180
CAGACCACCC  CGGTCCAGAC  GGTGACCATA  GTACAACAGG  CACCTCTAGG  TCAACACCAG         240
CTACCAATAA  AAACTGTAAC  ACAAAACGGC  ACTCACGTGG  CATCAGTCCC  CACTGCGGTC         300
CACGGCCAGG  TGAACAATGC  CGCGGCGAGT  CCTTTGCACA  TGTTGGCAAC  ACACGCATCC         360
GCATCGGCCT  CCCTGCCCAC  AAAGCGCCAC  AACGGTGACC  AGCCGGAGCA  GCCGGAGCTG         420
AAGCGGATCA  AGACAGAAGA  CGGCGAG                                                447
```

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
GCTTTGCTAT  CTAAGGATCA  C                                                       21
```

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
GATGCCTTCC  ATAGTCTCCA                                                          20
```

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
CTACTGTAAT  CCTAACACCT  G                                                       21
```

( 2 ) INFORMATION FOR SEQ ID NO:10:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

GGACTTAGAC TTTATGCCTG      20

( 2 ) INFORMATION FOR SEQ ID NO:11:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

GGCAGATACC TAATGACGAT      20

( 2 ) INFORMATION FOR SEQ ID NO:12:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

GACCATACAT AGTTTGCCCA      20

( 2 ) INFORMATION FOR SEQ ID NO:13:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

CTAACACCTG CCACTCTAGT      20

( 2 ) INFORMATION FOR SEQ ID NO:14:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

CTTGTGTGCT CTGCTGTCTC      20

( 2 ) INFORMATION FOR SEQ ID NO:15:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

CTAACACCTG CCACTCTAGT      20

( 2 ) INFORMATION FOR SEQ ID NO:16:

( i ) SEQUENCE CHARACTERISTICS:

```
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:16:
```

CTGATTCTTG GATACCACAG A                                                                                        21

COMPOSITIONS AND USES THEREOF IN THE DIAGNOSIS OF PSORIASIS

BACKGROUND OF THE INVENTION

1. Field of the Invention

The present invention relates generally to the field of molecular genetic tools for screening biological samples, as well as methods for using them in the mapping of chromosomes and in the diagnosis of disease. The invention also relates generally to the field of pharmaceutical compositions that include as an active agent preparations directed to a particular gene. More particularly, the invention concerns molecular genetic probes and methods of using them in detecting a genetic polymorphism associated with a familial psoriasis susceptibility locus in a human biological sample.

2. Description of the Related Art

Psoriasis is a chronic inflammatory dermatosis that affects ~2% of the population. It is characterized by hyperproliferation of epidermal cells and inflammation resulting from infiltration of activated T helper cells and mononuclear cells and release of pro-inflammatory cytokines (Menter and Barker, 1991; Barker, 1991). It may also be associated with arthritis and can present as a severely inflammatory dermatosis in patients with acquired immunodeficiency syndrome (AIDS) (Duvic, 1990). The symptoms of psoriasis include sharply defined erythematous patches covered with a distinctive scale, hyperproliferation of the epidermis, incomplete differentiation of keratinocytes and dermal inflammation. Clinical variants of psoriasis include erythroderma, seborrheic, inverse, guttate, and photosensitive psoriasis, pustular variants and Reiter's disease.

The role of immunomodulation in psoriasis is supported by the pharmacological action of drugs such as cyclosporine. For example, inhibition of the synthesis of interleukin-2 prevents the proliferation of T cells and thus their release of cytokines. Mediators of inflammation play a role in the immunoregulation of psoriasis. Currently available methods for treatment include topical therapy, phototherapy, photochemotherapy and systemic therapy and provide, at best, only temporary relief. Topical glucocorticoids are most commonly prescribed as the initial treatment of psoriasis for their anti-inflammatory, antimitotic and antipruritic effects. However, their efficacy is often short term. Crude coal tar is a complex mixture of thousands of hydrocarbon compounds and affects psoriasis by enzyme inhibition and antimitotic action. Although effective, tar stains the skin and has an odor. Anthralin (dithranol) is used topically and inhibits enzyme metabolism and reduces epidermal mitotic turnover. Remission may last for weeks to months. Phototherapy and photochemotherapy entailing the administration of the photosensitizing drug methoxsalen are only temporarily effective, as psoriasis recurs months after this treatment is discontinued. This recurrence indicates that the therapy is palliative rather than curative. Long-term consequences are altered immunologic effects and an increased risk of carcinogenesis.

Methotrexate is the most commonly administered systemic cytotoxic agent for widespread psoriasis. Contraindications are numerous and after withdrawal, psoriatic symptoms may be more severe than during earlier episodes. Hydroxyurea, etretinate, cyclosporine, and AZT are also systemic medications used for the control of psoriasis and all have serious side effects. Clearly, an understanding of the pathogenesis of psoriasis remains an important challenge in dermatologic medical treatment.

Associations between psoriasis and certain human lymphocyte antigen (HLA) alleles have been described. This factor has been used to support the hypothesis that psoriasis is a T cell-mediated, autoimmune disorder (Bos, 1988; Baadsgaard et al., 1990). The presence of the HLA-Cw6 allele may predispose to psoriasis because there is a strong association between age of onset, family history, and the presence of HLA-Cw6, B-13 and B-w-57 (Henseler and Christophers, 1985; Christophers and Henseler, 1989). The relative risk of HLA-Cw6 carriers developing psoriasis is 20 (Talkainen et al., 1980). This HLA association between psoriasis and HLA indicates that certain HLA alleles are more frequent in psoriasis patients than in controls. Loci are "linked" when they do not assort independently at meiosis.

Monozygotic twins have significantly higher concordance rates of disease generally than dizygotic twins (Brandrup et al., 1978; Watson et al., 1972). Psoriasis has also been reported to aggregate in some families (Pietrzyk et al., 1982; Kervonen et al., 1976; Civatte et al., 1977; Espinoza et al., 1980). The aggregation of psoriasis in families suggests that psoriasis can be inherited as an autosomal dominant trait with penetrance values of 10 to 50%. About 30% of psoriasis patients have a first degree relative with the disease (Barker, 1991).

Additional predisposing loci unlinked to HLA are beginning to be identified for some diseases previously described as HLA-associated. One example is insulin-dependent diabetes mellitus where there is evidence that the insulin gene on chromosome 11p can confer susceptibility (Bell et al., 1964; Thompson et al., 1989; Julier et al., 1991; Spielman et al., 1993). Evidence collected by the present inventors of predisposing loci other than HLA in autoimmune diseases encouraged the present invention and has resulted in the identification of markers linked to psoriasis susceptibility.

Some of the problems associated with mapping common genetic diseases have been described (Hall et al., 1990). When only a small proportion of cases are due to bona fide inherited susceptibility, some apparently familial cases may be present only because the disease is so common. Other factors that may confound a linkage analysis are incomplete penetrance of the trait in susceptible individuals and variations in phenotypic expression of the trait (which may depend on age, gender, modifier genes, and environmental trigger factors such as antecedent streptococcal infection [Baker et al., 1993]). The existence of more than one major gene accounting for psoriasis (genetic heterogeneity) is likely, again decreasing the ability to detect linkage by pooling LOD scores (the logarithm of the likelihood ratio for linkage) from different kindreds.

A need continues to exist in the medical arts for preparations and techniques for both diagnosing and treating psoriasis and psoriasis-like conditions that have less severe side effects and are more effective in treating the source of the disease.

SUMMARY OF THE INVENTION

The present invention addresses the foregoing and other drawbacks of the prior art by identifying an inheritable genetic polymorphism that is useful in the diagnosis of forms of psoriasis in linked families. The genetic tools useful in this diagnosis may also be useful in the preparation of therapeutic agents significantly more patient compatible and without the side effects associated with conventional psoriasis treatments.

Prior to the present Invention, no evidence existed demonstrating an association between psoriasis and a defective interleukin gene. The present inventors screened the entire human genome by genotyping families with psoriasis using PCR™-based microsatellite markers. A positive LOD score was found in some of the families with markers on chromosome 17q indicating that these markers were in close proximity to a gene for psoriasis susceptibility. Further analysis localized the gene to the distal end of chromosome 17q. A computer search of genes localized to chromosome 17 allowed the present inventors to identify the ILF gene as a possible candidate gene. ILF was chosen as a candidate based on its location within a region identified by linkage analysis and its regulation of the expression of IL2. The probability of ILF as having a psoriasis susceptibility locus was further strengthened when a polymorphism was found within an intron of the gene. By using this polymorphism as a genetic marker on a Southern blot analysis the present inventors were able to show there were no recombinations between the disease gene and this marker in one of the large linked families. This result indicates that the marker is very close to the disease gene, or perhaps actually within the disease gene. No one but the present inventors has proposed ILF as a possible candidate gene for psoriasis nor is there any clinical evidence prior to the present invention which would have implicated this gene in psoriasis.

The present invention identifies a psoriasis susceptibility locus found in a number of patient samples that characterizes a specific location of a psoriasis gene. This gene is not associated with any gene for the HLA antigens. The invention overcomes several drawbacks inherent in the prior art by providing a nucleic acid probe for the detection of a polymorphism within a psoriasis susceptibility locus among linked families afflicted with psoriasis. In one embodiment, this locus maps to the distal region of human chromosome 17q in some patients afflicted with familial psoriasis, and on chromosome 4 in other families with psoriasis afflicted members. The psoriasis susceptibility locus is contemplated by the present inventors to provide a marker useful in the detection of a genetic alteration in a patient nucleic acid sample that is related or is the gene encoding ILF or IL8. The invention is therefore also anticipated to be useful as an important molecular genetic tool in the characterization and screening of patients for psoriasis.

A second locus was identified by the present inventors as another probable psoriasis susceptibility locus. This locus, on chromosome 4, is near an interleukin 8 gene. The locus was found by using microsatellite marker D4S400 in a continuation of the genome-wide search. An LOD score of 4.11 (odds of 10,000:1 in favor) at a recombination factor of 0.036 with the microsatellite marker D4S400, which has been mapped to chromosome 4 between 4q13 and 4q21 has also been obtained that identifies the psoriasis susceptibility locus in these families at chromosome 4. Several of the families that did not show linkage to chromosome 17 appeared to be linked at this locus. Therefore, interleukin 8, which maps to this same region (4q13 and 4q21), is a candidate gene for a psoriasis susceptibility locus on chromosome 4q.

In one particularly preferred aspect, the present invention provides a method for screening a family for psoriasis susceptibility. In particular, the method employs the use of a familial psoriasis susceptibility locus that identifies a marker for psoriasis susceptibility within a family. Accordingly, the method comprises obtaining a nucleic acid sample from a patient having psoriasis and a member of the patient's family that does not have psoriasis. The sample obtained from the patient's family member without psoriasis provides a control sample according to the claimed method. The method next comprises identifying a family specific allele of a polymorphism that is present in the patient nucleic acid sample that is not present in the control sample, the polymorphism being linked with a gene for interleukin enhancer binding factor or interleukin 8. This step results in the identification of a familial psoriasis susceptibility locus in the particular family being screened. The method further comprises preparing a probe hybridizing to the psoriasis susceptibility locus and screening the nucleic acid samples (preferably DNA) from members of the patient's family with the probe so as to provide a method for screening a family for familial psoriasis susceptibility.

According to the methods of the present invention, the probe is fashioned so as to hybridize to the particular chromosomal region wherein the particular familial form of the allelic polymorphism is found to exist. By way of example, this probe may include a sequence that hybridizes to the distal region of human chromosome 17q, or instead to the region between 4q13 and 4q21 of chromosome 4q, or instead to a region of chromosome 4p2. The present inventors have determined the existence of a psoriasis susceptibility marker at the distal portion of chromosome 17q, as well as to chromosome 4p2 and chromosome 4q by observing a positive LOD score among psoriasis patients within a family with markers at chromosome 17q and also with markers on chromosome 4p and 4q These positive LOD scores indicated to the present inventors that these markers were in close proximity to the gene for psoriasis susceptibility. As used in the description of the present invention, the term "positive" LOD score is used to indicate any LOD score for linkage that is a value of 3 or greater. Such a positive LOD score is recognized by those of skill in the art as demonstrating a positive linkage with a particular gene related to a disease.

In one embodiment, the psoriasis susceptibility locus has a recombination factor with genetic marker D4S400 of about 0.036 and an LOD score of 4.11. This particular form of the locus maps to chromosome 4 between 4q13 and 4q21. In still another embodiment, the probe includes a sequence that hybridizes to a distal region of human chromosome 17q or chromosome 4q. With regard to the locus as associated with chromosome 17q, the method of the present invention may be further defined as employing a probe that includes a sequence complimentary to a region 5' of an intron containing a Pvu II or a Pst I polymorphism within the ILF gene and a sequence complementary to region 3' to the intron. These probes may be defined as having a length of between 18 bp and about 1 million bp. More preferred lengths of the probe are between about 400 bp and about 2000 bp, or even more preferably about 450 bp. By way of example, such an about 450 bp probe is provided in SEQ ID NO:6. A specific example of such a probe is provided in the sequence illustrated at SEQ ID NO:4, having a length of 20 bp (complementary to the region 5' of the intron at 17q), and SEQ ID NO:5, also having a length of about 20 bp (complementary to the 3' region of the intron). The psoriasis susceptibility locus may be further defined as located distal to genetic marker D17S784 of chromosome 17q. Even more generically, the psoriasis susceptibility locus may be defined as located within an intron of the gene encoding for interleukin enhancer binding factor at human chromosome 17q. The locus may also be further described as a Pvu II polymorphism or as a Pst I polymorphism.

Turning to another aspect of the present invention, a psoriasis susceptibility locus itself is disclosed. This locus may be defined as located within an intron sequence of human chromosome 17q, said locus further defined as located distal to genetic marker D17S784 of human chromosome 17q. This intron sequence may be even more particularly defined as being within a gene encoding for interleukin enhancer binding factor.

The present invention also provides a nucleic acid molecule as a composition of matter, the molecule having a sequence of any one of SEQ ID NO:1–16, or a fragment thereof from about 15 to about 100 nucleotides in length. However, any nucleic acid segment of the molecule lying within this range, such as 18, 20, 25, 30, 35, 40, 50, 60, 70, 80 or 90 nucleotides in length that are sufficient to provide specific hybridization to the distal end of human chromosome 17q, this region corresponding to the psoriasis susceptibility locus described above, are anticipated as within the scope of the present invention. Of course, nucleic acid sequence complementary to said sequences are also anticipated as part of the present invention.

The present invention also provides a cDNA capable of detecting a genetic polymorphism identifying a psoriasis susceptibility locus within family members of an afflicted patient. The cDNA of this invention may be further described as mapping within an about 11 cM region distal to a genetic marker D17S784 of human chromosome 17q. The cDNA so described may be prepared according to a process comprising the steps of obtaining yeast artificial chromosomes containing human sequences from chromosomes 17q distal to genetic marker D17S784, obtaining a cosmid library containing human sequences from chromosome 17q, selecting cosmids having sequences represented in the yeast artificial chromosome library, obtaining tissues specific primary cDNA's, selecting a cDNA from the primary cDNA's having sequences represented in the selected cosmids, and screening the selected cDNA for sequences that map to human chromosome 17q, the cDNA having a sequence that maps and hybridizes to a region distal to genetic marker D17S784 of human chromosome 17q. The cDNA of the present invention may be even further defined as having a sequence that upon hybridization to human DNA, detects a sequence altered from a wild type sequence in a sample DNA from a patient with a familial form of psoriasis.

Obtaining yeast artificial chromosomes according to the above described process may be more particularly defined as including the steps of annealing sequences of DNA having between about 15 to about 40 nucleotides from a region of human chromosomes 17q distal to genetic marker D17S784 with a human chromosome 17 YAC library and selecting the human chromosome YACs that bind the sequences. Further, the step of selecting cosmids according to the aforedescribed process may be further defined as including the steps of obtaining probes from the yeast artificial chromosomes using inverse repeated sequence polymerase chain reaction probes, annealing the probes with human DNA having repetitive sequence, incubating the annealed probes with the cosmid library, and selecting cosmids which bind the annealed probes.

By way of example, the tissue-specific primary cDNA's described in the foregoing process may be obtained from epithelial cells, activated T-cells or keratinocytes as preferred sources. However, it is expected that other sources of tissue specific primary cDNA's may also be used, such as placental cells and the like in the processes and compositions, as well as in the practice, of the many aspects encompassed by the present invention.

In one preferred aspect, the step of selecting a cDNA according to the described process may include the steps of adding linkers to the primary cDNA's to form Tinkered cDNA, amplifying the Tinkered cDNA, labeling the cosmids to form labeled cosmids, hybridizing labeled cosmids to the Tinkered cDNA, and isolating linkered cDNA that hybridizes to the labeled cosmids. Furthermore, the step of screening selected cDNA for sequences that map to human chromosome 17q may be further described as including the step of hybridizing the selected cDNA to DNA samples from psoriasis affected members in genetically linked psoriasis families. Screening may also be achieved by sequencing the selected cDNA and corresponding cDNA from affected members in psoriasis linked families.

It is anticipated that the various forms of the probes and identified regions of the present invention may be used in a variety of utilities. For example, as the present inventors have determined that the sequences map to a highly polymorphic region of human chromosome 17q, the probes fashioned and found to correspond to this region may be employed in linkage analysis studies of human DNA. The probe may also be useful in hybridization studies of human chromosome 17. A particular practical utility of the claimed probes includes the use of the described probes in the identification of the presence of human chromosome 17 in a patient for clinical analytical applications.

The present invention also provides a method for detecting a genetic polymorphism in chromosome 17q distal region. The method in a most particularly preferred embodiment comprises preparing a probe that includes a sequence that hybridizes to a highly polymorphic region at the distal end of human chromosome 17q, contacting a DNA sample isolated from a human tissue with the probe for a sufficient amount of time to allow for the specific hybridization of the sample DNA to the probe under stringent hybridization conditions, conditions of high salt, high temperature, or both, as well known to those of skill in the art, and determining the presence of specific hybridization between the sample DNA and the probe, wherein in the presence of specific hybridization of the probe and the sample DNA provides for the detection of a genetic polymorphism at the distal end of human chromosome 17q.

The present invention also discloses a gene mapping to a highly polymorphic region at the distal end of human chromosome 17q. This gene is defined as including a psoriasis susceptibility locus, the psoriasis susceptibility locus having a recombination fraction with a genetic marker D17S784 of 0.04 and a LOD score of at least 6 with the marker D17S784. The psoriasis susceptibility locus which lies within this gene is further described as other than a human lymphocyte antigen locus, therefore distinguishing the gene from previously described HLA related genes.

Another specific embodiment of the present invention defines a psoriasis gene for a familial form of psoriasis comprising a gene mapping to the distal end of human chromosome 17q. This gene is further described as having close proximity or being within, particularly within an intron, of the gene encoding for an interleukin enhancer binding factor. The close proximity of the psoriasis gene to the interleukin enhancer binding factor gene correlates with a finding of increased levels of some interleukins found in patients that has been observed to result in symptoms similar to psoriasis. A polymorphism in the psoriasis gene so described indicates an inherited germ line mutation in the patient nucleic acid sample that is related to a familial form of psoriasis. The psoriasis gene may be further defined as being located within an intron region of the gene encoding for interleukin enhancer binding factor, said intron region being located within a region of the interleukin binding factor gene sequence flanked by a sequence as defined by SEQ ID NO: 4 and SEQ ID NO: 5.

The term distal region, as used in the description of the present invention relates to the 17q region in which the polymorphism was found for this invention, this region being between marker D17S802 and the telomere (end) of the chromosome 17q. This particular region is also characterized by the present inventors to have a high degree of polymorphism.

The following abbreviations are used throughout the present description of the present invention:

cDNA: DNA copied off an mRNA template by reverse transcriptase
CEPH: Centre d'etude du polymorphisme humain collaborative genetic mapping of the human genome
cM: centimorgan, or 1/100th of a Morgan
Contig: series of clones having ordered, overlapping inserts
DGGE: denaturing gradient gel electrophoresis
D17S74: 74th single copy segment of DNA to be isolated from human chromosome 17 (term for a locus)
ILF: interleukin enhancer binding factor
kb: kilo-base (1,000 bases)
IRS-PCR: inverse-repeated sequence PCR
LOD: logarithm of the odds ratio
LOH: loss of heterozygosity
Morgan: a unit of recombination (there are 33 Morgans in the human genome)
PCR: polymerase chain reaction
SSCP: single-strand conformation polymorphism
STS: sequence tagged site
VNTR: variable number of tandem repeats
YAC: yeast artificial chromosome

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1A:
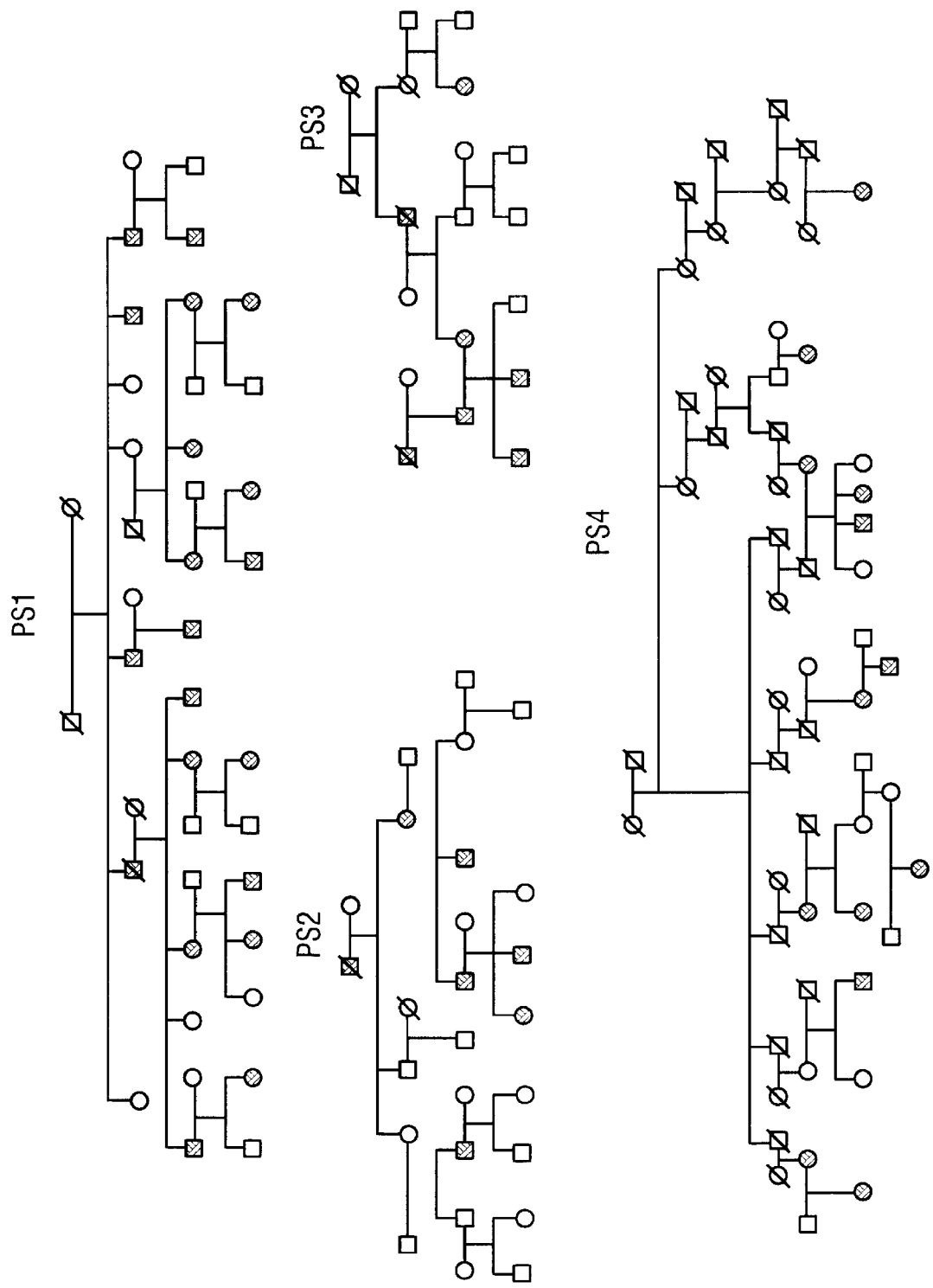
FIG. 1A and FIG. 1B describe psoriasis families participating in this study. Circles, females; squares, males; batched symbols, individuals with psoriasis. Deceased individuals are represented by diagonal lines through symbols. The average age of onset of psoriasis in these families is shown in parenthesis: PS1 (18), PS2 (6), PS3 (17), PS4 (29), PS5 (23), PS6 (unknown), PS7 (21), and PS8 (21). Three families had affected members who had developed the disease in infancy (PS1: four of the 17 members for whom the ages of onset were known; PS2: three of the six affected members; PS5: one of the eleven affected members for whom the ages of onset were known).

Genes for psoriasis susceptibility were localized to the distal region of human chromosome 17q and to chromosome 4 as a result of a genome-wide linkage analysis with polymorphic microsatellites and eight multiply affected psoriasis kindreds. With one large kindred a maximum two-point LOD score of 4.65 at 4% recombination with D17S784 was obtained using a model of dominant inheritance. Penetrance in this family is estimated to be greater than 80%. When all eight kindreds were considered the combined maximum two-point LOD score with D17S784 was 5.51 at 11% recombination. Heterogeneity testing indicated that a psoriasis susceptibility locus in 55% of these families was linked to distal 17q. Multipoint linkage analysis suggested that a locus responsible for familial psoriasis susceptibility resides within an about 11 cM region between D17S784 and D17S928. Despite previous descriptions of associations with HLA-alleles and psoriasis, no linkage with DNA markers within, nor flanking the HLA cluster of genes was detected in the families. The ability to detect linkage confirms that some forms of familial psoriasis are due to molecular defects at a single major genetic locus, inherited in an autosomal dominant fashion. Mapping the genes for psoriasis susceptibility is expected to identify those genes responsible for sporadic psoriasis in the general population.

The DNA segments disclosed herein find utility as probes or primers in nucleic acid hybridization embodiments. In addition, they are particularly useful as a tool for human chromosomal mapping, as it is demonstrated that the probes hybridize to the distal region of human chromosome 17q. It is contemplated that oligonucleotide fragments of these DNA segments that have at least a length that is sufficient to provide specific hybridization with a target DNA of human chromosome 17q will have utility as such a molecular probe for human chromosome 17q. For example, such fragments having a length of between about 10, 15 or 18 nucleotides to about 20, or to about 30 nucleotides, will find particular utility. Longer sequences, e.g., 40, 50, 80, 90, 95, 100, even up to full length, are even more preferred for certain embodiments. Lengths of oligonucleotide of at least about 18 to 20 nucleotides are well accepted by those of skill in the art as sufficient to allow sufficiently specific hybridization so as to be useful as a molecular probe, as described by Lathe (1985), which reference is specifically incorporated herein by reference for this purpose.

The ability of such nucleic acid probes to specifically hybridize to sequences present in the distal region of chromosome 17q will enable them to be of use in a variety of other embodiments as well. For example, the probes may be used for screening a sample for a normal complement of chromosomes by providing a probe that will identify the presence of human chromosome 17 in a patient sample. In addition, the probes are anticipated to have utility in detecting the presence of polymorphisms that may be responsible for at least some forms of inheritable diseases that are characterized by genes or gene changes in human chromosome 17q. Other uses are also envisioned, including the use of the sequence information for the preparation of mutant species primers, or primers for use in preparing other genetic constructions.

Nucleic acid molecules having stretches of 10, 18, 20, 30, 50, 60, 65 or even up to and including 100 nucleotides or so, complementary to any one of SEQ ID NO: 1–16, have utility as hybridization probes. Primers or probes having a nucleotide length of about 18 nucleotides are recognized by those of skill in the art to provide highly specific hybridization to a target sequence, particularly where the probe has a low $K_b$ value (Lathe, [1985]). These probes are useful in a variety of hybridization embodiments, such as Southern, Northern blotting and PCR™ in connection with assaying chromosome 4p and 4q and the distal portion of chromosome 17q for disease related polymorphisms. The total size of the fragment, as well as the size of the complementary stretches, will ultimately depend on the intended use or application of the particular nucleic acid segment. Smaller fragments will generally find use in hybridization embodiments, wherein the length of the complementary region may be varied, such as between about 10, 18, 20 or 30 and about 50, 60, 70, 80, 90 or 100 nucleotides, or even full length according to the complementary sequences one wishes to detect.

The use of a hybridization probe of about 18 to 20 nucleotides in length allows the formation of a duplex molecule that is both stable and selective (Lathe, [1985]). Molecules having complementary sequences over stretches greater than 18 or 20 bases in length are generally preferred, though, in order to increase stability and selectivity of the hybrid, and thereby improve the quality and degree of specific hybrid molecules obtained. One will generally prefer to design nucleic acid molecules having gene-complementary stretches of 20 to 30 nucleotides, or even longer where desired. Such fragments may be readily prepared by, for example, directly synthesizing the fragment by chemical means, by application of nucleic acid reproduction technology, such as the PCR technology with two priming oligonucleotides of U.S. Pat. No. 4,603,102 (herein incorporated by reference), or by introducing selected sequences into recombinant vectors for recombinant production.

Accordingly, the nucleotide segments of the invention may be used for their ability to selectively form duplex molecules with complementary stretches of chromosome 4 or of the distal region of chromosome 17q or cDNAs from that region or to provide primers for amplification of DNA or cDNA from this region. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02M–0.15M NaCl at temperatures of about 50° C. to about 70° C. Such selective conditions tolerate little, if any, mismatch between the probe and the template or target strand, and would be particularly suitable for isolating genes.

Of course, for some applications, for example, where one desires to prepare mutants employing a mutant primer strand hybridized to an underlying template or where one seeks to isolate tissue specific-encoding sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as in PCR for detection of expression of corresponding genes, as well as in embodiments employing a solid - phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantified, by means of the label.

Longer DNA segments will often find particular utility in the recombinant production of peptides or proteins. DNA segments which encode peptide antigens from about 15 to about 50 amino acids in length, or more preferably, from about 15 to about 30 amino acids in length are contemplated to be particularly useful, as are DNA segments encoding entire tissue specific proteins. DNA segments encoding peptides will generally have a minimum coding length on the order of about 45 to about 150, or to about 90 nucleotides. DNA segments encoding full length proteins may have a minimum coding length in the order of about 400 nucleotides for a protein.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

It will be understood that this invention is not limited to the particular nucleic acid sequences of SEQ ID NO's: 1–16, and particularly is intended to encompass at least nucleic acid sequences that are hybridizable to these sequences, (complementary to these sequences), or are functional sequence analogs of these sequences. DNA segments prepared in accordance with the present invention may encode biologically functional proteins or peptides. Functionally equivalent proteins or peptides having variant amino acid sequences may arise as a consequence of codon redundancy and functional equivalency which are known to occur naturally within nucleic acid sequences and the proteins thus encoded. Functionally equivalent proteins or peptides may alternatively be constructed via the application of recombinant DNA technology, in which changes in the protein structure may be engineered, based on considerations of the properties of the amino acids being exchanged.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence (or, of course, its underlying DNA coding sequence) and obtain a protein with like or even counterveiling properties (e.g., antagonistic v. agonistic). It is thus contemplated by the inventors that various changes may be made in the sequence of SEQ ID NO. 1, 2 or 3 without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982). It is known that certain amino acids may be substituted for other amino acids having a similar hydropathic index or score and still result in a protein with similar biological activity. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant protein, which in turn defines the interaction of the protein with other molecules, for example, enzymes, substrates, receptors, antibodies, antigens, and the like. It is known in the art that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Mapping a Genomic Region Distal to D17S802 Encompassing a Psoriasis Susceptibility Locus The present example is provided to demonstrate the utility of the present invention in the identification of a genomic region having a psoriasis susceptibility locus, and thus the utility of the invention as a method for screening biological samples for psoriasis and for preparing therapeutic agents for the treatment of psoriasis and skin conditions related to psoriasis. This psoriasis susceptibility locus was identified in the present example to be within chromosome region 17q. However, a psoriasis susceptibility locus may also occur at other chromosome regions, such as 4p2 or 4q.

Figure 1B:
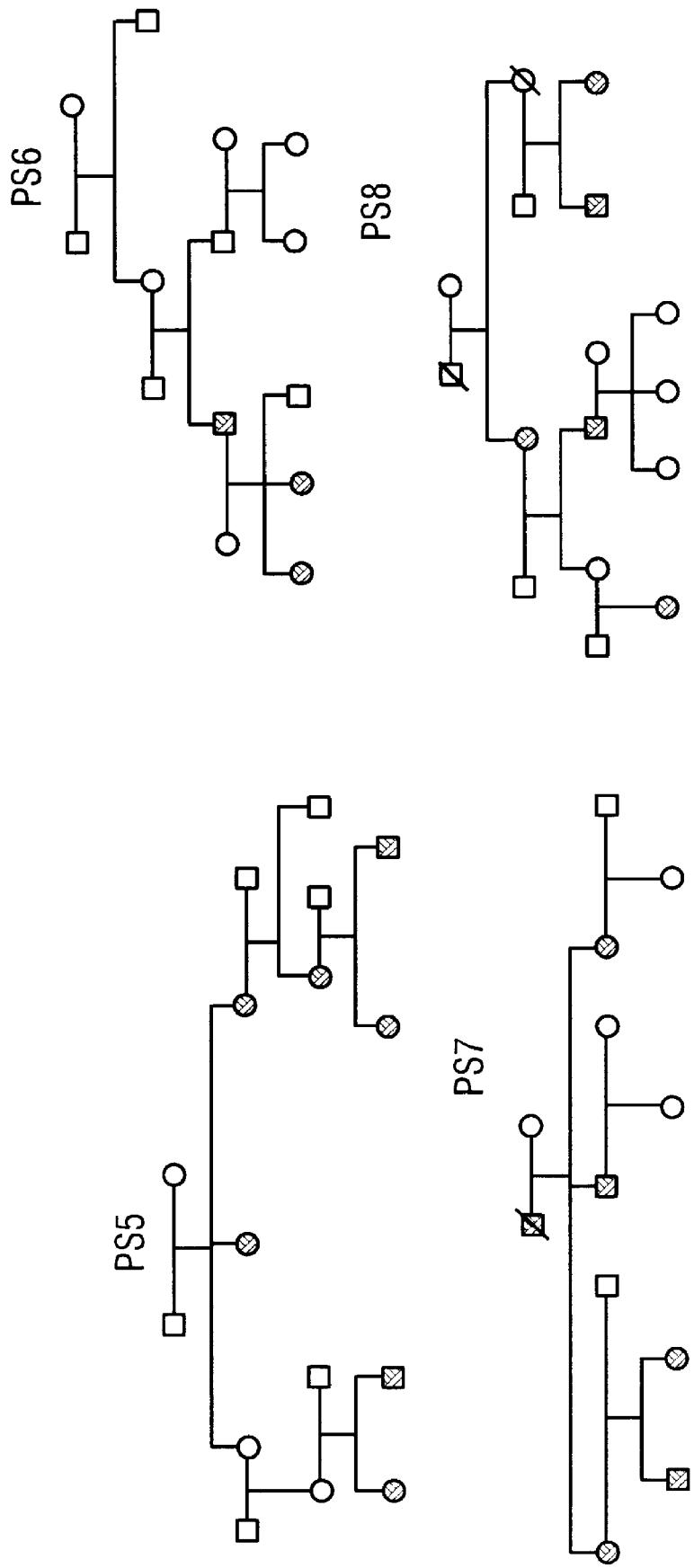
Figure 2A:
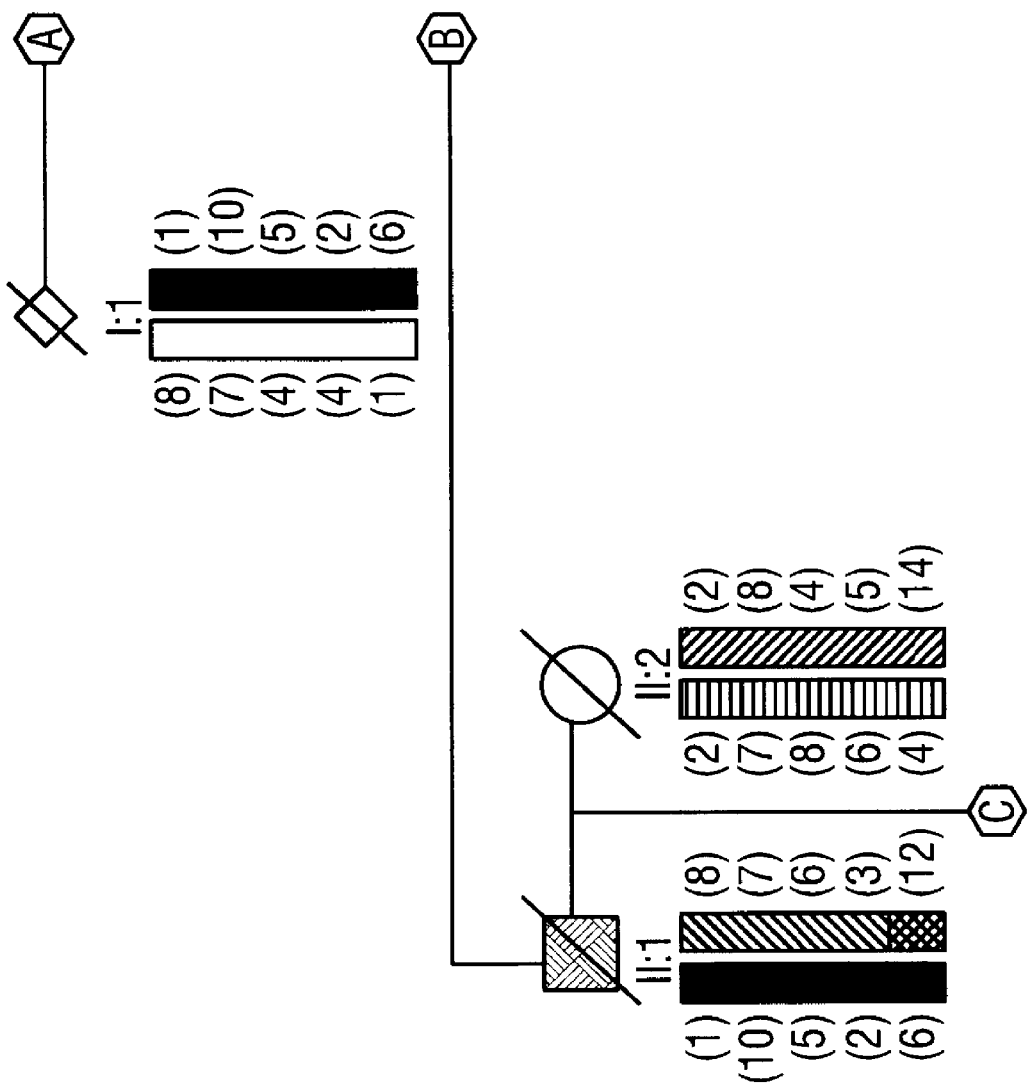
FIG. 2A, FIG. 2B, FIG. 2C and FIG. 2D show chromosome 17q haplotypes for family PS1. Symbols are as described for FIG. 1A and FIG. 1B. The haplotype harboring the psoriasis susceptibility gene is shown by a black bar. Loci (from top to bottom) for which genotypes are provided are as follows: D17S515, D17S785, D17S802, D17S784 and D17S928. Inferred genotypes are indicated in parenthesis. Uniparental disomy was detected in individuals II:6 and IV:9. Multipoint results are shown in FIG. 4.
Figure 2B:
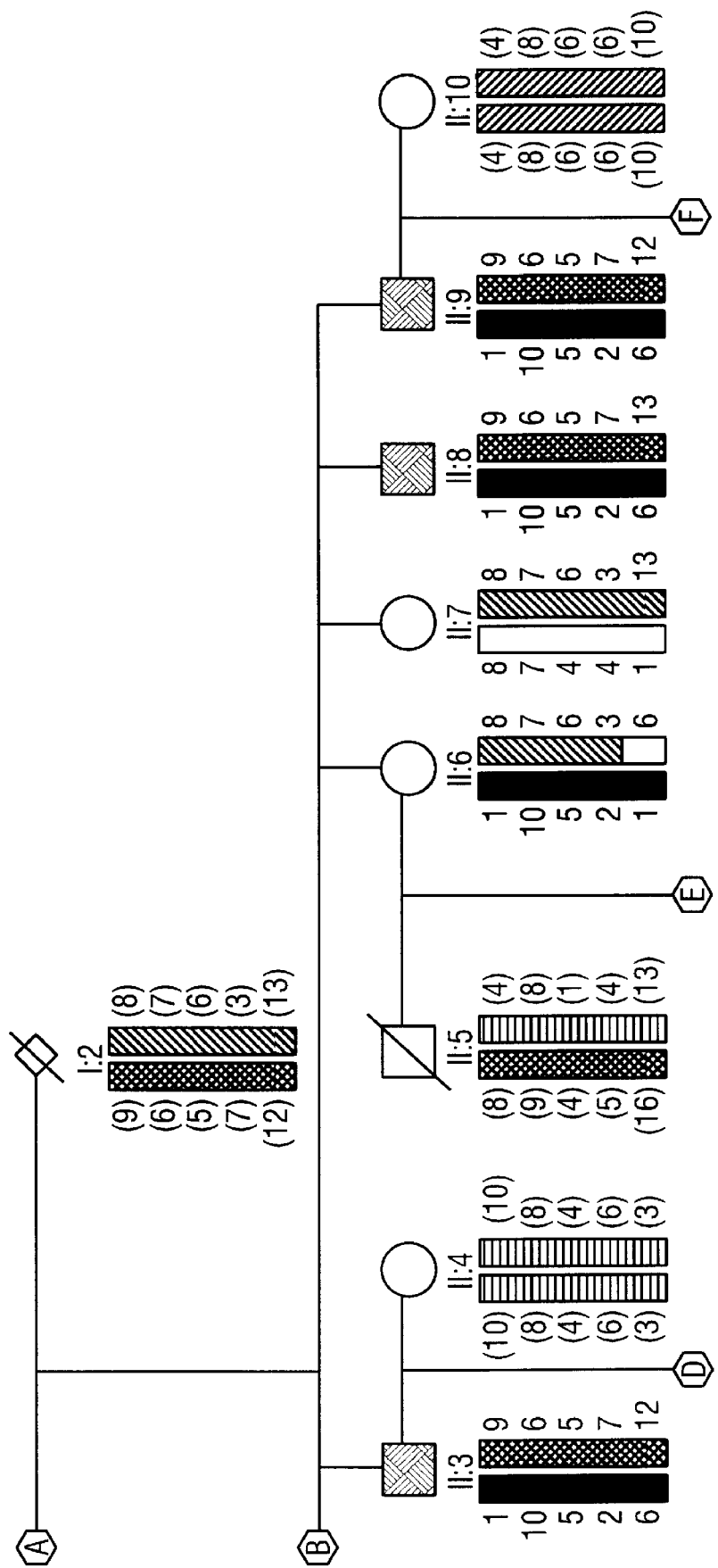
Figure 2C:
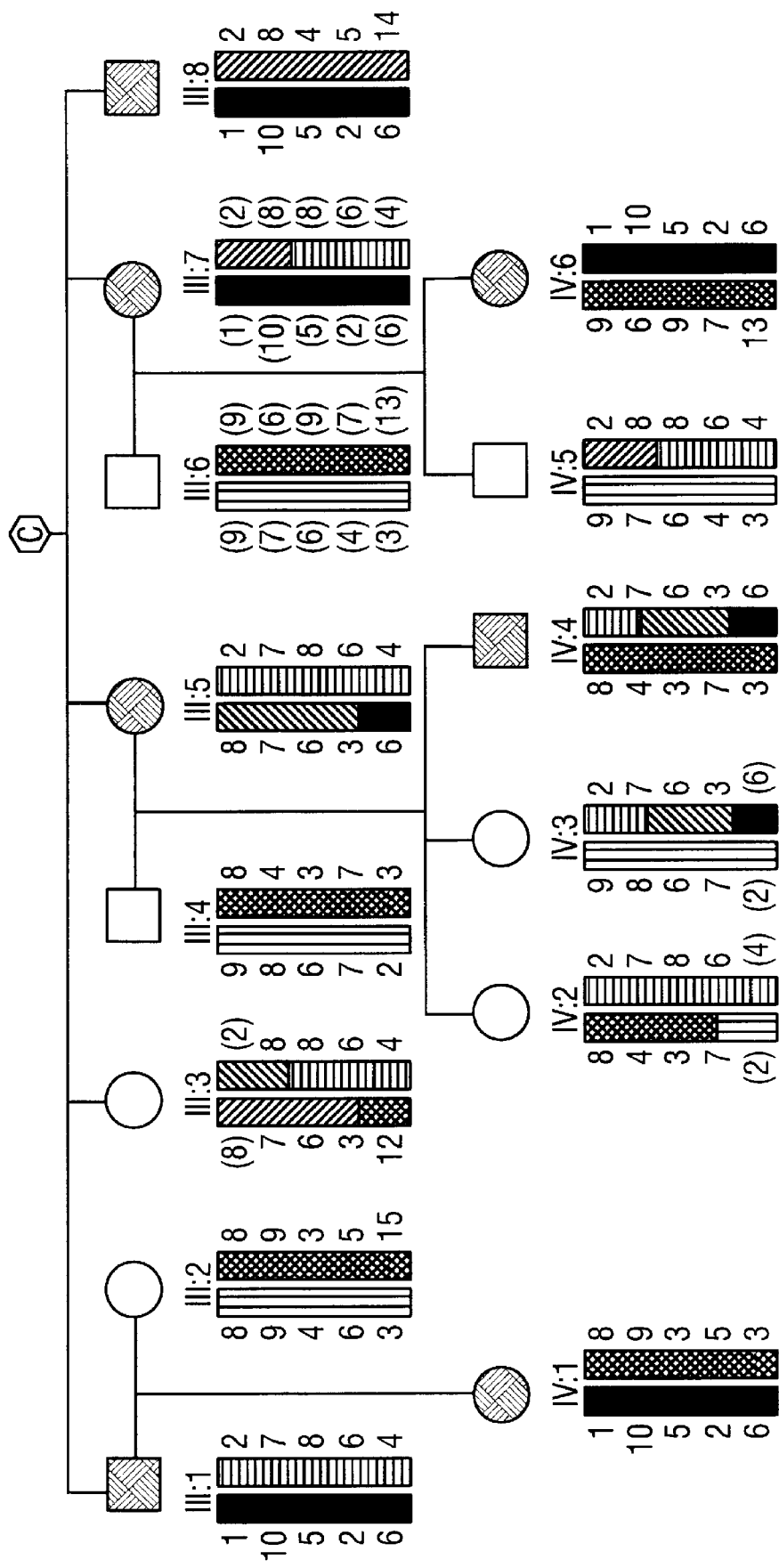
Figure 2D:
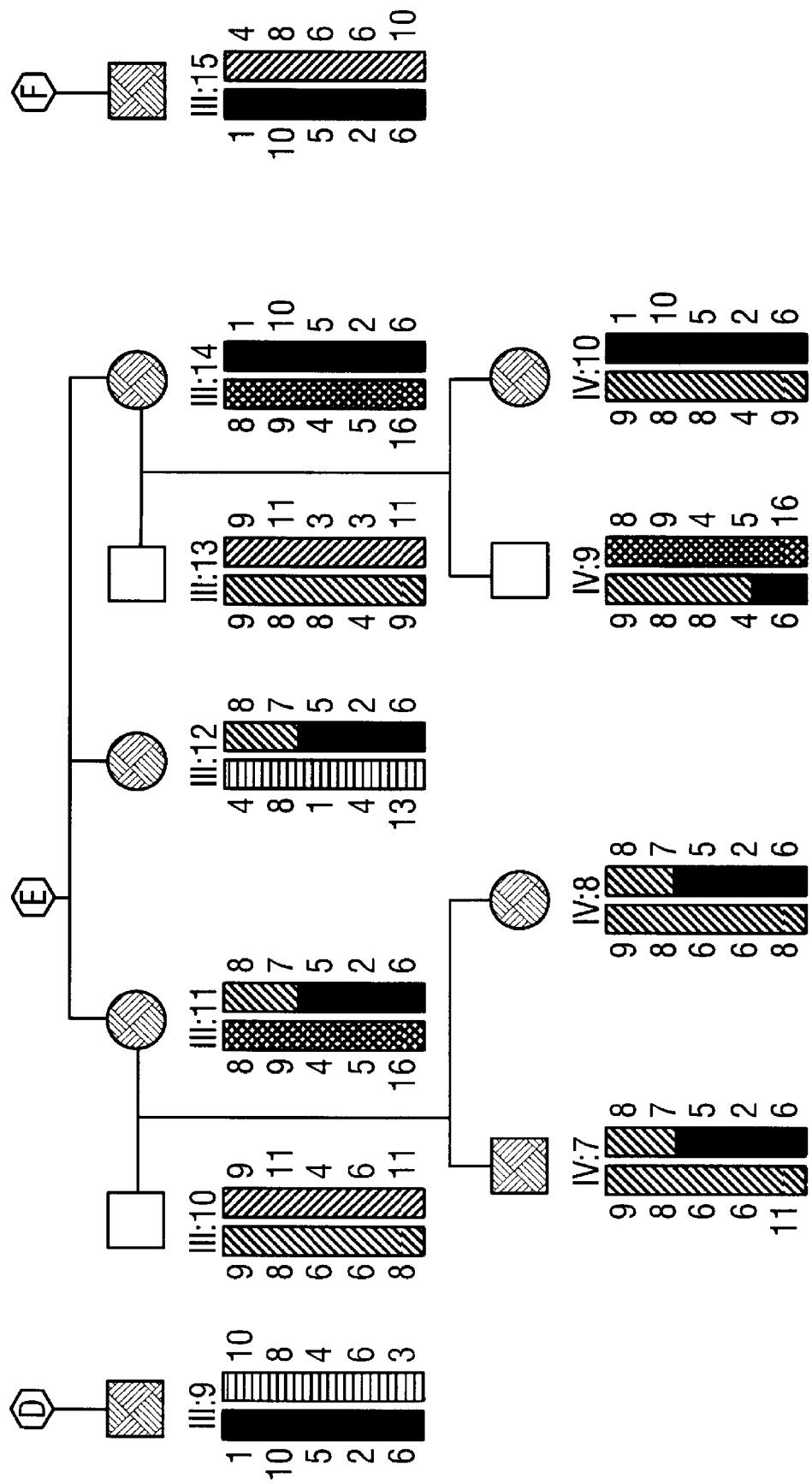

The present inventors conducted a genome-wide search for DNA markers cosegregating with a psoriasis susceptibility locus in eight multiply affected families with a total of 65 cases of psoriasis (FIG. 1A and FIG. 1B). All 151 participating relatives were Caucasian and sampled from 15 states of the United States. Presence or absence of psoriasis was based on standard clinical diagnosis of the disease determined from a thorough medical history and clinical evaluation obtained and analyzed on each patient. All patients were previously positively diagnosed as having a form of psoriasis known as plaque psoriasis using techniques well known to those of ordinary skill in the medical arts (see Menter and Barker, 1991). Informed consent was obtained from all family members available for venipuncture.

Lymphoblastoid cell lines were established by Epstein-Barr virus transformation of peripheral blood lymphocytes, and genomic DNA was isolated from these cells or from whole blood by phenolchloroform extraction as described (Feder et al., 1985).

A set of polymorphic microsatellites spanning the human genome (Bowcock et al., 1993; Beckmann et al., 1993; Weissenbach et al., 1992) and at an approximate resolution of 10 cM were selected with MultiMap (Malice et al., 1994). Polymorphic microsatellites were genotyped as described in Bowcock et al. (1993).

Because no adequate models previously existed for the inheritance of psoriasis, three different approaches were used to identify a DNA marker cosegregating with psoriasis susceptibility. The LOD score approach was first used and 14 different analyses were performed in which the mode of inheritance and the penetrance were varied. The second approach was an "affected-only" analysis of the first approach that was used to determined if nonaffected individuals could obscure potential linkage. This approach was independent of penetrance, and all individuals who were not coded as affected were recorded as unknown. The LINK-AGE software package (Lathrop et al., 1984) was used for these analyses. The third approach was the affected-pedigree-member (APM) method that does not depend on the mode of inheritance of the disease and was used because the results of the first two approaches are sensitive to inaccuracies in the assumed genetic model. The APM method does not necessarily trace the segregation of alleles with a disease in families, but tests for excess sharing of alleles at the marker locus among related affected individuals (Weeks and Lange, 1992). This allows one to evaluate allelic identity-by-state among affected individuals. The programs from the APM GENETICS PROGRAMS package (Weeks and Lange, 1992; Weeks and Lange, 1988) were used for this. For all analyses, marker allele frequencies were estimated from Centre d'Etude du Polymorphisme Humaine (CEPH) families.

After genotyping 69 polymorphic microsatellites, the present inventors obtained evidence of linkage with D17S784 [AFM044$_{xg}$3] (Wiessenbach et al., 1992) when psoriasis susceptibility was treated as a dominant trait. Pairwise LOD score data for the first approach for D17S784 and for additional linked loci (D17S785, D17S802, and D17S928) (Wiessenbach et al., 1992) are presented by family and are shown in Table 1.

TABLE 1

Pairwise chromosome 17 LOD score data by family. The population prevalence of psoriasis was assumed to be 1%. Penetrance = 0.99.

| | Recombination fraction | | | | | | | | |
|---|---|---|---|---|---|---|---|---|---|
| Family | 0.00 | 0.01 | 0.05 | 0.10 | 0.20 | 0.30 | 0.40 | $Z_{max}$ | θ |
| Locus D17S785 | | | | | | | | | |
| PS1 | −0.01 | 0.51 | 1.95 | 2.37 | 2.25 | 1.63 | 0.76 | 2.42 | 0.13 |
| PS2 | −4.57 | −2.30 | −1.20 | −0.72 | −0.32 | −0.13 | −0.04 | 0.00 | 0.50 |
| PS3 | −0.62 | −0.32 | 0.08 | 0.22 | 0.24 | 0.15 | 0.05 | 0.25 | 0.16 |
| PS4 | −0.15 | 0.00 | 0.28 | 0.39 | 0.38 | 0.24 | 0.08 | 0.40 | 0.14 |
| PS5 | −1.88 | −1.54 | −0.96 | −0.63 | −0.33 | −0.19 | −0.10 | 0.00 | 0.50 |
| PS6 | −3.63 | −1.66 | −0.92 | −0.60 | −0.29 | −0.14 | −0.05 | 0.00 | 0.50 |
| PS7 | 0.26 | 0.26 | 0.23 | 0.19 | 0.11 | 0.06 | 0.01 | 0.26 | 0.00 |
| PS8 | −1.10 | −0.81 | −0.38 | −0.18 | −0.03 | 0.01 | 0.01 | 0.01 | 0.30 |
| Total | −11.71 | −5.86 | −0.94 | 1.03 | 2.01 | 1.62 | 0.73 | 2.01 | 0.20 |
| Locus D17S802 | | | | | | | | | |
| PS1 | 0.76 | 4.47 | 4.76 | 4.52 | 3.65 | 2.60 | 1.16 | 4.77 | 0.04 |
| PS2 | −5.59 | −3.12 | −1.54 | −0.79 | 0.16 | 0.05 | 0.07 | 0.07 | 0.36 |
| PS3 | 0.84 | 0.82 | 0.72 | 0.60 | 0.38 | 0.18 | 0.05 | 0.84 | 0.00 |
| PS4 | −2.45 | −1.19 | −0.32 | −0.01 | 0.14 | 0.12 | 0.05 | 0.15 | 0.22 |
| PS5 | −3.36 | −1.67 | −0.97 | −0.59 | −0.18 | 0.00 | 0.05 | 0.05 | 0.40 |
| PS6 | −3.10 | −1.82 | −0.98 | −0.59 | −0.24 | −0.10 | −0.04 | 0.00 | 0.50 |
| PS7 | −3.12 | −2.53 | −1.60 | −1.10 | −0.60 | −0.33 | −0.14 | 0.00 | 0.50 |
| PS8 | −4.06 | −3.21 | −1.86 | −1.16 | −0.50 | −0.19 | −0.04 | 0.00 | 0.50 |
| Total | −20.07 | −8.25 | −1.79 | 0.88 | 2.49 | 2.23 | 1.16 | 2.54 | 0.23 |
| D17S784 | | | | | | | | | |
| PS1 | 1.36 | 5.07 | 5.32 | 5.03 | 4.06 | 2.79 | 1.30 | 6.33 | 0.04 |
| PS2 | −0.39 | 0.03 | 0.68 | 0.93 | 0.97 | 0.73 | 0.35 | 1.00 | 0.15 |
| PS3 | −0.80 | −0.49 | −0.10 | 0.04 | 0.08 | 0.04 | −0.01 | 0.09 | 0.17 |
| PS4 | 2.30 | 2.24 | 2.02 | 1.74 | 1.17 | 0.65 | 0.25 | 2.30 | 0.00 |
| PS5 | 0.37 | 0.37 | 0.42 | 0.52 | 0.59 | 0.50 | 0.30 | 0.59 | 0.19 |
| PS6 | −3.04 | −1.37 | −0.68 | −0.40 | −0.16 | −0.06 | −0.02 | 0.00 | 0.50 |
| PS7 | −4.96 | −3.70 | −2.16 | −1.42 | −0.74 | −0.39 | −0.17 | 0.00 | 0.50 |
| PS8 | −2.98 | −2.47 | −1.69 | −1.09 | −0.58 | −0.29 | −0.11 | 0.00 | 0.50 |
| Total | −8.13 | −0.32 | 3.91 | 5.35 | 5.39 | 3.97 | 1.59 | 5.70 | 0.15 |

TABLE 1-continued

Pairwise chromosome 17 LOD score data by family. The population prevalence of psoriasis was assumed to be 1%. Penetrance = 0.99.

| Family | Recombination fraction | | | | | | | $Z_{max}$ | θ |
|---|---|---|---|---|---|---|---|---|---|
| | 0.00 | 0.01 | 0.05 | 0.10 | 0.20 | 0.30 | 0.40 | | |
| | | | | D17S928 | | | | | |
| PS1 | 2.26 | 2.23 | 2.08 | 1.88 | 1.42 | 0.91 | 0.35 | 2.26 | 0.00 |
| PS2 | −1.75 | −1.15 | −0.25 | 0.17 | 0.44 | 0.39 | 0.18 | 0.45 | 0.23 |
| PS3 | −0.70 | −0.71 | −0.67 | −0.35 | −0.13 | −0.07 | −0.05 | 0.00 | 0.50 |
| PS4 | −1.88 | −1.52 | −0.79 | −0.32 | 0.03 | 0.08 | 0.05 | 0.08 | 0.30 |
| PS5 | −1.01 | −0.76 | −0.32 | −0.11 | 0.04 | 0.05 | 0.02 | 0.05 | 0.26 |
| PS6 | 0.17 | 0.17 | 0.14 | 0.12 | 0.07 | 0.03 | 0.01 | 0.17 | 0.00 |
| PS7 | −4.21 | −3.92 | −3.06 | −2.16 | −1.15 | −0.58 | −0.22 | 0.00 | 0.50 |
| PS8 | −2.49 | −2.12 | −1.32 | −0.85 | −0.38 | −0.15 | −0.03 | 0.00 | 0.50 |
| Total | −9.61 | −7.78 | −4.09 | −1.62 | 0.34 | 0.66 | 0.31 | 0.66 | 0.30 |

For family PS1, a maximum two-point LOD score of 5.33 at 4% recombination with D17S784 was obtained with the first model (at 99% penetrance), and a maximum two-point LOD score of 3.33 at 4% recombination with D17S784 was obtained with the "affecteds-only" model. When the inverse square root weighting function was used, the multilocus APM analysis indicated that there was a highly significant excess of haplotypes that were shared among affected members of the PS1 family (empirical P value<0.0001). All three approaches supported linkage to markers at the distal region of 17q.

No segregation analysis has been performed for psoriasis susceptibility; consequently, there was no estimated penetrance value to use for the calculations, and LOD scores were initially calculated over a variety of penetrance values. Considering just the large linked family (PS1) in which evidence for linkage was strongest, there were 21 individuals with the susceptibility haplotype and 20 of these were affected, giving a penetrance estimate of ~95%. However, four unaffected members in this family were not sampled for genotyping. If one or more of these unaffected individuals did harbor the susceptibility haplotype, the penetrance estimate would be less. In this family, varying the penetrance from 60 to 99% or varying the frequency of the disease allele did not affect the results significantly. Considering all eight families, the maximum two-point LOD score was obtained when a penetrance of 80% was used ($Z_{max}$=6.04, θ=0.10). However, there was no significant difference in the conclusions when penetrance values of 60% ($Z_{max}$=5.96, θ=0.08) or 99% ($Z_{max}$=5.70, θ=0.15) were used. The "affecteds-only" analyses gave similar results, though the LOD scores were smaller (for the eight families combined $Z_{max}$=4.04, θ=0.10).

To refine the location of the psoriasis susceptibility locus, the present inventors constructed a genetic map of polymorphic microsatellites from this region and used it as a baseline map for multipoint linkage analysis of family PS1. The chromosome 17 genetic map was constructed with data from the CEPH (v6-0) database and data from the eight psoriasis families. The map was generated and verified with the "build" and "flips 8" options of the CRI-MAP program (Lander and Green, 1987); CRI-MAP, 2–4; P. Green, Washington University School of Medicine, Genetics Department, St. Louis, Mo. All markers could be placed with odds greater than $10^6$:1.

The order and sex-average recombination fractions between the marker loci are as follows: centromere-D17S785-0.04-D17S802-0.10-D17S784-0.11-D17S928-telomere. Because of computational limitations, multilocus linkage analyses were performed after recording the data to reduce the number of marker alleles. The present inventors obtained a peak multipoint LOD score of 6.42 between D17S784 and D17S928 (6.6% distal to D17S784 and 5.1% proximal to D17S928), suggesting that this psoriasis susceptibility gene lies within this interval. However, the next most likely region, distal to D17S928, was only 16:1 times less likely. The odds against placement proximal to D17S802 were greater than 1000:1. Location scores obtained under the assumption of different recombination fractions in males and females lead to the same conclusion regarding the location of the disease locus. The data obtained with the "affecteds-only" model were in close agreement, giving a peak LOD score of 4.41 for tight linkage to D17S928 (no recombination). Chromosome 17q haplotypes for family PS1 are shown in FIG. 2A, FIG. 2B, FIG. 2C and FIG. 2D. Multipoint linkage analysis with families PS6, PS7, and PS8 yielded only negative LOD scores.

Figure 4:
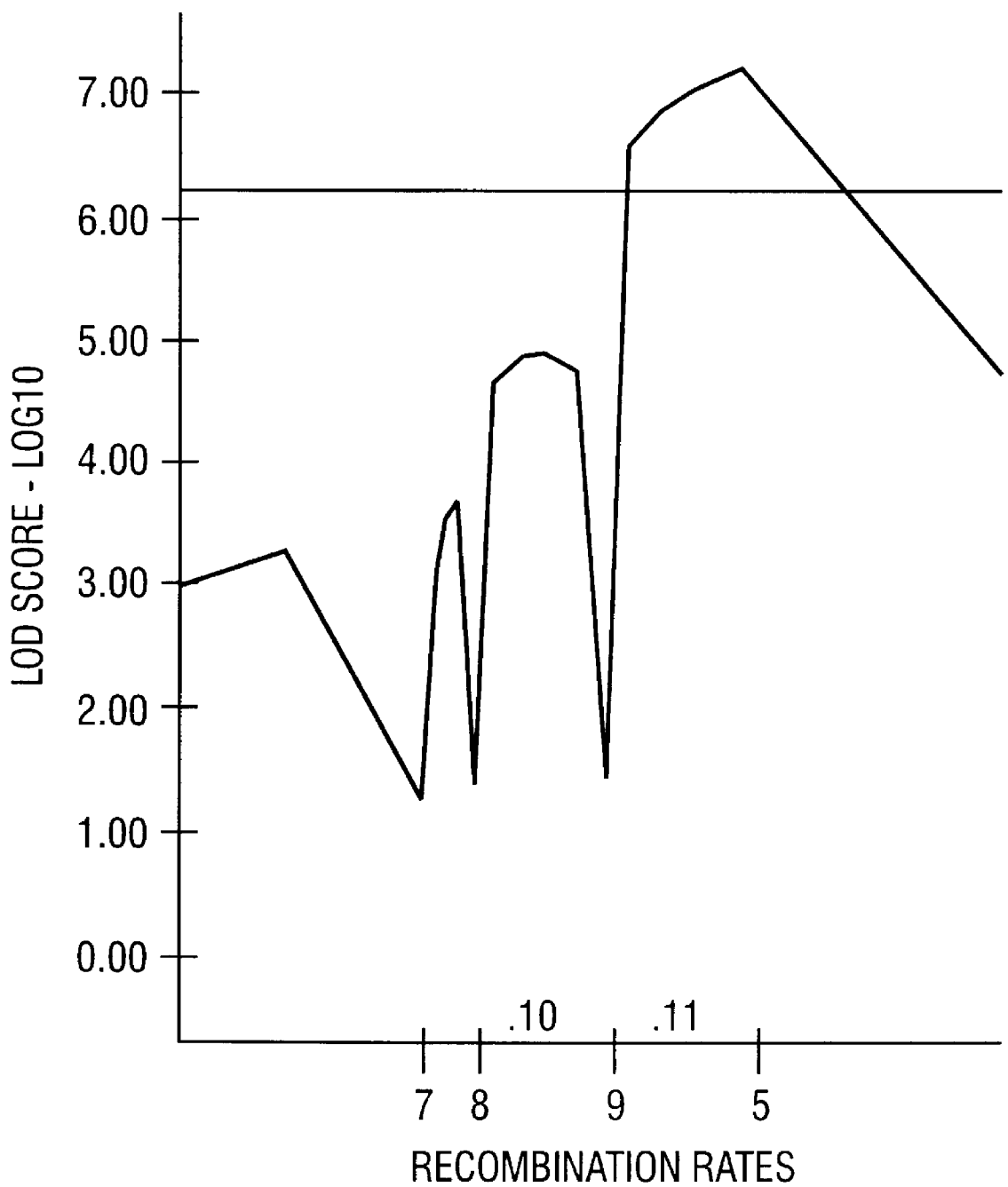
FIG. 4 shows a multipoint map showing the most likely location of the psoriasis susceptibility locus. The baseline map was constructed with genotypes of family PS1. Locus 7:D17S785; 8:D17S802; 9:D17S784; 5:ILF. No recombinants were detected with ILF and the psoriasis susceptibility locus. A maximum LOD score of 7.23 indicates a 10 million to one odds that a gene for psoriasis susceptibility is tightly linked to ILF or is ILF.

Further analyses with a polymorphic marker located within the ILF indicated that this psoriasis susceptibility locus is located very close to, or within the ILF gene (FIG. 4). Chromosome 17q haplotypes for family PS1, and including the ILF1 polymorphic marker are shown in FIG. 2A, FIG. 2B, FIG. 2C and FIG. 2D.

The admixture test, as implemented in the HOMOG program (Ott, 1991), was significant when tested against multipoint LOD score data (α=0.50). Hence, there was evidence for heterogeneity with 50% of the families being linked. Families PS1 and PS2 showed strong evidence consistent with linkage (posterior probabilities>0.97), whereas families PS4 and PS5 showed less evidence (posterior probabilities 0.94 and 0.76). Families PS3, PS6, PS7, and PS8 appear to be unlinked (posterior probabilities<0.20). When only families PS1, PS2, PS4 and PS5 were considered, the combined maximum two-point LOD score for linkage between D17S784 and a psoriasis susceptibility locus was 8.44 at 6% recombination with the first model and 5.67 at 2% recombination with the second model. There were no apparent differences in clinical presentation observed in the linked and unlinked families.

EXAMPLE 2

Lack of Association of Linked Psoriasis Susceptibility with HLA

The present example demonstrates that there was no evidence for linkage of psoriasis susceptibility with polymorphic microsatellites within and flanking the HLA cluster, or with class II haplotypes (Fernandez-Vina et al., 1991; a,b) for any of the families. Because of the previously reported associations of psoriasis susceptibility to HLA alleles and in particular to HLA-CW6, the association of psoriasis susceptibility with this allele was examined with polymerase chain reaction sequence-specific oligonucleotide probes in the families (PCR-SSOP).

Typing of HLA-C locus alleles was accomplished by PCR amplification and single-stranded oligonucleotide probe (SSOP) hybridization. PCR primers CIP-283D (GCGACGCCGCGAGTCCGATAGG, SEQ ID NO:1) and CIP-IN3 (CCCCACTGCCCCTGGTACCCGCGCGCT, SEQ ID NO:2) were used to generate a fragment of ~700 base pairs (bp) by PCR amplification. This fragment extends from codon 46 to 180 and includes the second half of exon 2, intron 2, and exon 3 of the HLA class C genes. The presence of HLA-Cw6, and the related allele –c1. 10, was identified by SSOP hybridization with CI-326 (CTCCAGTGGATGTATGGCT, SEQ ID NO:3) that detects a codon for Met at residue 97 specific for these two alleles. An additional set of 14 SSOPs spanning other polymorphic codons (70 to 75, 76 to 81, 91 to 97, 95 to 101, 111 to 117, and 151 to 157) was used to distinguish Cw6 from c1.10 and to genotype the other HLA-C locus alleles. Amplified genomic DNA from 8 homozygous B cell lines carrying HLA-Cw6 and from 10 B cell lines carrying other C-locus alleles was used to monitor the specificity of the SSOP.

Only two of the families in which psoriasis susceptibility was unlinked to 17q (PS6 and PS7) yielded empirical P values for excess sharing of the HLA-Cw6 allele of 0.027 and 0.004, respectively (for significance empirical P value ~0.0001 implies a LOD score of 3 [(Ott, 1991]). These empirical P values were generated with 10,000 replicates and, though not significant, suggest that psoriasis susceptibility in families PS6 and PS7 may be associated with HLA-Cw6.

EXAMPLE 3

The Distal Region of 17q contains an ILF Gene

The present example provides a candidate gene for the psoriasis susceptibility locus, the ILF gene. The ILF-2 gene (Li et al., 1992) may be considered an equivalent gene as a candidate for the psoriasis susceptibility locus.

Linkage mapping is used in the study of human diseases to identify regions likely to contain disease genes. These regions can then be isolated with physical mapping approaches such as the cloning of the region in a series of overlapping yeast artificial chromosomes, converting these to cosmids, and using these to select genes by means of a variety of approaches which include direct hybridization to complementary DNA libraries, exon trapping (Sucider et al., 1991; Duyk et al., 1990), and direct selection (Lovett et al., 1991; Parimoo, 1991). Occasionally linkage mapping reveals several highly probable candidate genes within the mapped region.

A gene involved in the activation of T cells was shown to lie within this distal region of 17q. This is ILF, or interleukin enhancer binding factor which, in addition to an inducible T lymphocyte factor (NFAT), binds to purine-rich regions of the interleukin-2 (IL-2) and human immunodeficiency virus (HIV) promoters (Li et al., 1991, 1992). This ILF gene was determined by the present inventors to be a good candidate gene for the psoriasis susceptibility locus.

In order to ascertain whether affected members in families showing linkage to 17q harbor alterations in ILF that may result in an inability to repress IL-2 transcription, nucleic acid sequences of the ILF gene were used to probe for polymorphisms in the genome sequence emcompassing the ILF gene (Li et al., 1992). Inappropriate expression of IL-2 would result in the inflammatory cascade and hyperproliferation characteristic of lesional skin.

EXAMPLE 4

A Highly Informative Polymorphism Lies Within the ILF Gene on Human Chromosome 17q The present example demonstrates the utility of the present invention for identifying a highly polymorphic locus with many alleles that characterizes a psoriasis susceptibility locus present in affected members from 17q-linked families.

In searching for restriction fragment length variants, the present inventors identified a segment of this ILF gene that is highly polymorphic, and is likely to be due to variable numbers of a tandem repeat that cluster at telomeres.

Primers IL4D-1 (CCAGCGAACACGTACACTGT, SEQ ID NO:4) and ILF-13 (CTCGCCGTCTTCTGTCTTGA, SEQ ID NO:5) were selected from the ILF sequence (position 1634-2080, Li et al., 1992) and were used to amplify cDNA obtained from the RNA of transformed lymphocytes from affected family members. This resulted in a 446 bp PCR amplification product that was used to probe Southern blots.

Southern blotting was carried out as follows: 2.5 µg DNA was digested with Pst I and subjected to agarose gel electrophoresis. Hybridization was at 65° C. overnight in aqueous hybridization solution.

Figure 3:
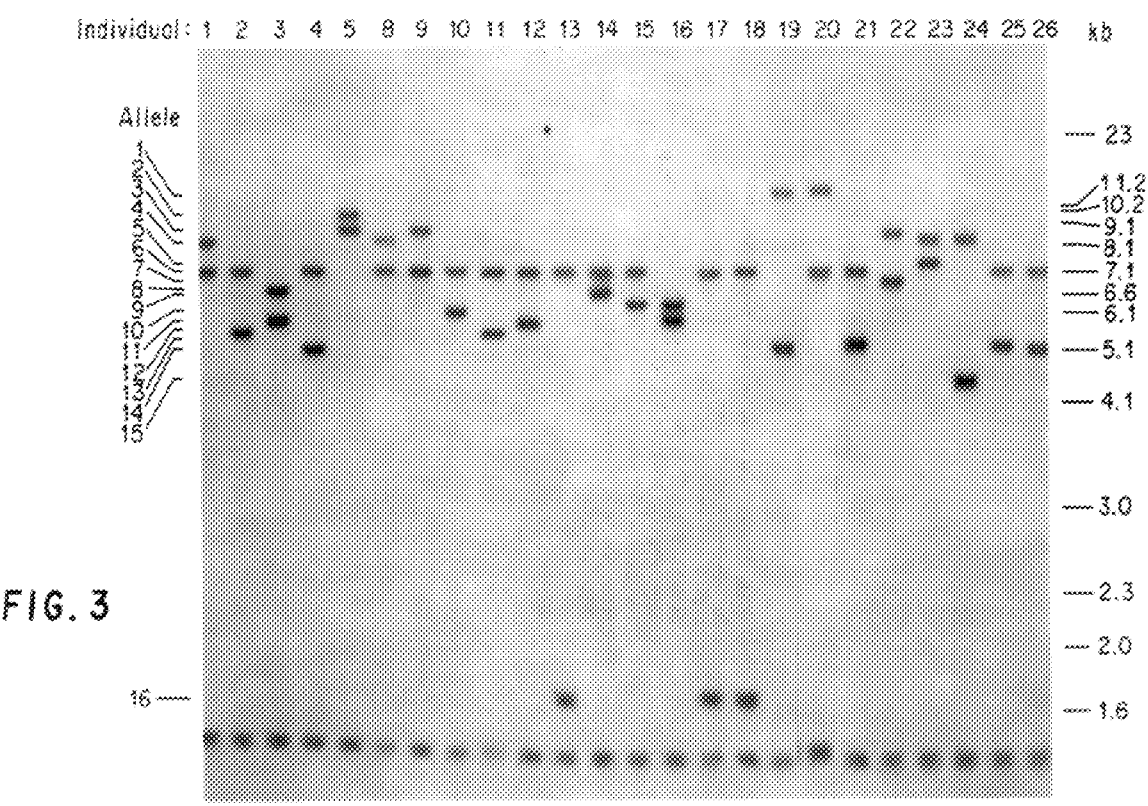
FIG. 3 shows a Southern blot of a typical pattern of alleles as described in Example 4.

A polymorphic locus with many alleles was detected with several enzymes. Most preferably, the enzymes useful for these purposes are Pst I and Pvu II. Allele lengths, which ranged from 1.6 kb to 11.2 kb with Pst I, and the number of enzymes that revealed this polymorphism, suggested that it was due to variable numbers of a tandem repeat (VNTR), with a repeat unit of approximately 290 bp. The typical pattern of alleles seen is shown in FIG. 3. FIG. 2A, FIG. 2B, FIG. 2C and FIG. 2D show a revised haplotype of psoriasis family PS1, with ILF alleles.

To refine the location of the psoriasis susceptibility locus, the present inventors constructed a genetic map of this region and used it as a baseline map for multipoint linkage analysis of a psoriasis susceptibility locus in family PS1 (FIG. 4). No recombinants were detected at ILF, suggesting that it is very close to, or at the psoriasis susceptibility locus. This provides further evidence that altered ILF may result in psoriasis susceptibility.

The polymorphism described herein is useful in confirming or disproving linkage of this gene to psoriasis susceptibility in families. It is also useful for association studies between this gene and psoriasis susceptibility. In the family described here, no recombinants were detected between psoriasis susceptibility and this gene; although a de-novo mutation was detected in two affected individuals (i.e. a spontaneous mutation frequency of 15%). In each case the mutation was of paternal origin. In one individual this mutation may have arisen as a result of crossing-over between the two paternal alleles since the size of the new allele was the average of the size of the two paternal alleles. All affected individuals in this family had inherited a "6" allele, which was intermediate in size between the largest and smallest allele that was observed.

This Pvu II RFLP having at least four alleles in family PS1 and being highly informative for linkage studies is being used to place ILF on the chromosome 17q linkage map by analyzing CEPH families for this marker and performing linkage analyses with other chromosome 17 markers. Psoriasis families are also being genotyped for this RFLP.

EXAMPLE 5

Linkage to Chromosome 4 and a Candidate Gene IL-8

The present example provides a locus on chromosome 4 identified by the present inventors as a region of DNA containing a probable psoriasis susceptibility locus. The locus was found by using microsatellite markers in a genome-wide search. Several of the families that did not show linkage to chromosome 17 had positive LOD scores and appear to be linked at this locus. An LOD score of 4.11 (odds of 10,000:1) at a recombination factor of 0.36 was found with the microsatellite marker D45400 that has been mapped to chromosome 4 between 4q13 and 4q21. This 4q locus is near the interleukin 8 gene which has been mapped to the same region, therefore, the interleukin 8 gene is a candidate gene for a psoriasis susceptibility locus.

The genomic sequence of the IL-8 gene is described in Mukaida et al. (1989). Primers of SEQ ID NOs 7–16 were used to amplify each of the four exons of the IL-8 genomic sequence and part of the non-coding 5' sequence. The resulting probe will be used to sequence the IL-8 gene from psoriasis affected and normal individuals.

EXAMPLE 6

ILF1 Involvement in Psoriasis Susceptibility

The present example provides for an analysis of the ILF sequence in affected and unaffected family members. The alternatively spliced exons of ILF2 and ILF3 will also be analyzed (Li et al., 1992). If an alteration is detected from the known sequence of ILF1 or the alternatively spliced counterparts, its frequency will be determined in normal controls from the same family and from the same population. An alteration in 17q linked affected members that occurs rarely or is lacking in unaffected members provides evidence that ILF is a psoriasis susceptibility gene.

Northern and Southern blots with RNA/DNA from linked affected family members and normal controls will be prepared and hybridized with ILF probes to determine if an altered transcript or major rearrangement can be detected that is specific to linked and affected family members. If any rearrangement is detected, the molecular defect will be determined by direct sequencing from genomic DNA. This may require the development of PCR systems that amplify this gene from genomic DNA.

The present inventors have a genomic clone containing the ILF gene, and intronic sequences flanking ILF exons can be determined by direct sequencing of the genomic clone with PCR primers specific to the cDNA. If a molecular defect is detected, the gene will be examined from sporadic cases of psoriasis, either from RNA (cDNA) obtained from blood cells, or from genomic DNA.

A polymerase chain reaction may be carried out as follows: 33 ng total human genomic DNA is amplified by PCR. Reactions are performed in a 20 $\mu$l volume with 0.25 $\mu$M of each oligonucleotide primer, 0.5 units TaqI polymerase (Promega), 0.25 $\mu$M spermidine, and 200 $\mu$M each of DATP, dGTP, dTTP, and dCTP is added to the standard PCR buffer. One 5'-labeled oligonucleotide ($10^4$ cpm) is included in the PCR reaction. Samples are overlaid with mineral oil (DNase and RNase-free; Sigma) and amplified for 30 cycles of 30 seconds (s) at 94° C., 30 s at 55° C., and 1 min at 72° C., followed by 7 min at 72° C.

A defect may also lie within the promoter or another regulatory region of the ILF1 gene. A 5' RACE approach will be used to identify the transcription start site of the gene, and a sequencing primer will be designed close to this region to sequence through the promoter site in cosmid or bacteriophage DNA containing this region of the gene. This region will then be analyzed by PCR amplification and direct sequencing in affected family members to search for mutations.

EXAMPLE 7

Identification of a YAC Contig within the Distal Region of Chromosome 17q

The present example provides for a YAC contig encompassing a psoriasis susceptibility locus. The linked region currently spans a distance of 11 cM. Although this is likely to represent 11,000 kb in interstitial regions of the chromosome, recombination at telomeres is often inflated, and a distance of 11 cM may correspond to 1/10th of its average distance 1,100 kb. It may therefore be possible to link up markers flanking the psoriasis susceptibility gene on CEPH mega-YACs, where the average insert size is 1,000 kb.

The present inventors will screen filters containing a gridded chromosome 17-specific cosmid library, prepared and supplied by Larry Deaven of the Los Alamos National Laboratory with oligonucleotides for D17S784 and D17S928 (or closer markers once identified), to identify cosmids containing these loci. These cosmids will then be mapped by fluorescence in situ hybridization (FISH), to determine the physical distance between them.

If these markers are reasonably close to one another (1–2 megabases), a series of overlapping YACs in this region will be identified from a total human genomic YAC library constructed at the Center for Genetics in Medicine at Washington University, St. Louis, Mo. (Brownstein et al., 1989) and two CEPH libraries, obtained from CEPH, Centre D'Etude Du Polymorphisme Humain, (Human Polymorphism Study Center), 27, rue Juliette Dodu, 75010, Paris, France, described by Albertsen et al., 1990 and Chumakov et al., 1992 with a PCR-based screening method previously described (Green et al., 1990). If the distance is larger than 1–2 megabases, the region will be refined genetically with additional markers in the interval. These markers will be genotyped in the linked families to determine if they lie between previously defined recombination breakpoints. Distances between these closer markers will be determined by FISH analysis as described above. Additional markers will be primarily polymorphic microsatellites detected with PCR amplification with oligonucleotide primers that flank the repeat. The development of such markers is described in Example 8.

DNA obtained from YACs is stored in microtiter plates. DNA from microtiter plates is pooled, and DNA from several microtiter plates are pooled into "mega-pools". These are made available for screening. Once a positive pool is identified, additional PCR reactions on DNA from individual microtiter plates is performed to determine the microtiter plate location of the positive YAC. Additional PCR reactions on YAC DNA from individual microtiter plate wells (or from rows and columns of microtiter plates) are performed to identify the YAC co-ordinate. The YAC stored on an archived microtiter plate at the corresponding address is used to make the YAC DNA.

Recent advances in physical mapping of the genome have resulted in YAC contigs spanning a large proportion of the genome. Information on those that have been reliably localized to chromosomes has been entered into the genome data-base and can be retrieved on the basis of which STS they contain. Currently, however, no CEPH YACs contain D17S784, therefore, the CEPH mega-YAC and smaller insert YAC libraries will be screened for YACs with D17S784 and D17S928. STSs will be polymorphic microsatellites, YAC end-clones, expressed sequence tags (ESTs) of genes (such as ILF), and if necessary be derived from other short sequences within YACs such as AluI-PCR™ products. STS content maps will be constructed for YACs to order and overlap YACs to form a contig. This approach also identifies chimeric YACs or YACs with rearrangements or deletions by identifying inconsistencies in STS order or content. This is a faster approach than FISH, although neither approach necessarily identifies small chimeric inserts or rearrangements. Chimeric or rearranged YACs will be excluded as subsequent reagents.

EXAMPLE 8

Generation of Additional Markers in the Psoriasis Susceptibility Region of 17q

Cosmids from within the psoriasis susceptibility region of 17q will be identified by IRS-PCR™ (described below) with somatic cell hybrid DNA or with radiation hybrid DNA containing portions of this region of chromosomes 17 (as determined by the presence of closely linked markers). By determining which hybrids overlap and which contain the psoriasis susceptibility gene, a minimum set of cosmids identified by hybrids containing this region will be identified.

Cosmids will be screened for "di-", "tri-" and "tetra-" nucleotide repeats, and those identifying such repeats will be used to develop PCR™-systems amplifying the repeats. Sequences flanking repeats will either be obtained from cosmid subclones, or with a scheme where cosmids are cleaved with a frequent cutter and ligated to a "bubble-linker" as described by Riley et al. (1990). PCR™ amplification with a vectorette primer and a repeat primer is then performed, and PCR™ products are sequenced. Primers flanking one side of the repeat are then synthesized and used as sequencing primers on cosmid templates in order to sequence through the repeat to the other side. Oligonucleotide primers flanking the repeats will then be designed, synthesized, and used in the PCR™ to amplify repeat containing regions that can be sized on sequencing gels. These newly developed markers will be genotyped in the chromosome 17q linked families, (and possibly in a subset of CEPH families exhibiting recombinants in this interval) to order markers and to refine the location of the psoriasis susceptibility gene.

EXAMPLE 9

Conversion of Somatic Cell Hybrids, Radiation Hybrids Microsatellites and YACs to Cosmids In general, it is easier to identify genes in clones which are smaller than YACS, such as cosmids. Cosmids have inserts of approximately 40 kb, and may be used in a variety of strategies to search for genes. To obtain a set of overlapping cosmid clones for the 4p, 4q or the distal 17q region, the YACs in the contig are used to generate probes for hybridization to gridded chromosome 17-specific cosmids, available from the Los Alamos National Laboratory, Los Alamos, N. Mex. The probes may be generated with "inverse repeated sequence PCR# (IRS-PCR™)." This procedure amplifies human DNA sequences between human-specific AluI repeats in the YAC DNA. AluI sequences are approximately 360 bp long, highly conserved, and distributed throughout the human genome in 300,000 to 500,000 copies (Jelinek, 1980). It is estimated that an AluI sequence occurs approximately at least once every 5–10 kb. Commonly called "AluI-PCR™" or "IRS-PCR™" (Ledbetter et al., 1990), this approach generates a variety of small fragments from the YAC inserts (for a review, see Nelson, 1989). Although such PCR™ fragments contain a small amount of AluI sequence, which is repetitive and would identify cosmids non-specifically, the AluI sequences are blocked before hybridization by being pre-annealed with human DNA rich in repetitive sequences. One problem with using IRS-PCR™ products as probes, is that regions poor in AluI sequences will be underrepresented, and this may result in gaps in the resultant cosmid contig.

Although the following step is not necessary for the isolation of cDNAs, it is performed with cosmids isolated with AluI-PCR™ probes derived from YACs from this region. Cosmids are ordered into a "contig" (a series of overlapping cosmids), by determining overlaps by hybridization. Repeats in cosmid DNA are "blocked" by hybridization with cold total human genomic DNA or COT1 DNA (BRL). Cosmids are then used as probes against other cosmids in the region (isolated by YACs from the region), to determine which overlapped.

Filters containing chromosome 17-specific cosmids arrayed at high density will be used to identify cosmids for D17S784 and D17S928. These will be used for a FISH analysis as described above. Once a YAC contig of a 1–2Mb region containing the gene has been constructed, YACs will be converted to cosmids. IRS-PCR™ (Ledbetter et al. 1990) will be performed for each YAC, and products will be pre-annealed with COT1 DNA and hybridized to high density chromosome 17-specific cosmid grids. Conversion to chromosome specific cosmids removes most of the complications of chimeric inserts in YACs (with the exception of the approximately 2% that are due to different inserts from the same chromosome) and covers some of the gaps that occur in some YACs.

IRS-PCR™ results in a random sampling of genomic sequences because of four limiting factors: (1) when performed with AluI primers, it samples only those regions that are AluI rich, (2) it will only amplify regions flanked by two IRS priming sites, (3) the repeat sequences must be in the correct orientation to each other, and (4) repeats must be reasonably close to generate a PCR# product. For this reason, inter-AluI PCR™ products are usually generated at intervals of approximately 50 kb, although AluI elements occur, on average, every 3 kb in AluI rich regions. To address some of these limitations, probes derived from YACs will be used with an approach described by Rosenthal and Jones (1990). A similar IRS-PCR™ approach will be used to obtain human-specific probes for somatic cell hybrids and radiation hybrids.

Cosmids will be "binned" according to the YACs that were used to detect them. DNA will be prepared from each cosmid, cleaved with 1–2 restriction enzymes, and subjected to agarose gel electrophoresis. Restriction fragment distributions will provide a crude cosmid fingerprint, and suggest which cosmids overlap. Cosmid inserts will be isolated, pre-annealed with COT1 DNA, and used as probes against dot blots of DNA from all other cosmids. These three approaches will result in a preliminary cosmid contig which can be used for gene isolation. When candidate genes on other chromosomes are found, the same approach as described for the identification of a psoriasis susceptibility gene on chromosome 17q will be followed, utilizing the appropriate chromosome-specific cosmid library.

EXAMPLE 10

Screening for Candidate Genes

Genes will be screened by (1) direct hybridization of repeat-blocked cosmids to cDNA libraries, (2) direct selection and (3) exon trapping.

Direct selection, as developed by Dr. Michael Lovett (Lovett et al. 1991; Lovett et al. 1993) appears to be a superb approach for identifying small pieces of genes. Sixty percent of cDNAs selected with a pool of cosmids map to the candidate region on the basis of hybridization to genomic DNA, somatic cell hybrid DNA, and to YACs and cosmids from the region using this approach.

The genomic substrate for selections will be YACs from the region or cosmid pools. cDNA sources will be linkered, primary cDNA, in particular, a linkered cDNA derived from activated T-cells and from keratinocytes. Different types of mitogens will be used for activating T-cells including streptococcal superantigens. Linkered cDNA derived from transformed keratinocytes from psoriatic and from normal individuals will be used and from whole skin of normal and psoriatic patients. Other cDNA sources are epithelia, placenta, thymus, liver, fibroblast and HeLa, in order to maximize the possibility of isolating the susceptibility genes. Another consideration in screening for genes is that if the gene one is searching for is transiently expressed, the stage at which the RNA is extracted from a particular tissue is critical since that RNA is used to make the cDNA.

Cosmids are the preferred reagent in the "direct selection by hybridization" strategy. This approach, pioneered by Lovett et al. (1991) and Parimoo et al. (1991), utilizes a genomic substrate such as cosmids, phage, YACs, or even whole chromosomal DNA. After blocking the human repeats in such a substrate, it is hybridized in solution to PCR™-amplified cDNA.

The number of cDNAs to be screened must be sufficiently large to be fairly certain that a low abundance cDNA will be identified. For this reason, at least $10^6$ cDNAs derived from a specific tissue source are screened. Primary (uncloned) cDNAs (a modification of the direct selection approach described by Morgan et al., 1992) chosen for direct selection of the cosmids for this invention will be activated T-cells, keratinocytes, epithelia, placenta, thymus, liver, fibroblast and HeLa cell primary cDNAs.

The above-named cDNAs are made by isolating mRNA from the specified tissue and, using reverse transcriptase, making cDNA copies of the RNA transcripts. Sambrook et al. provides methods that one skilled in the art may follow for the construction of cDNA. Sequence complexity of the starting mRNA population is retained by ligating oligonucleotide linkers to both ends of the primary (uncloned) cDNA.

Linkered cDNA is amplified using PCR™ in 50μl total volume. Aerosol, filter pipet tips are used for cDNA work. Control reactions are set up with primer and without cDNA to monitor contamination. Cycling conditions are as follows: 95° C. 2 minutes 1 cycle, 95° C. 1 minute, 55° C. 1 minute, 72° C. 2 minutes 35 cycles, 72° C. 7 minutes. The total yield of cDNA will be about 1–2μg from about 10 reactions of 50 μl. 5μl of PCR™ reaction is applied to a 1% agarose gel to estimate yield. The PCR™ reactions are pooled (about 450 μl) into a 1.5 ml Eppendorf tube, extracted with phenol/CHCl$_3$, CHCl$_3$, ethanol precipitated, washed in 70% ethanol, air dried, and resuspended in water (2 μg in 5 μl water). If more than one cDNA source is used and the total volume of cDNA exceeds 8 μl, the appropriate amounts of each cDNA are pooled and reprecipitated as above. Dry pellets are resuspended in 8 μl water.

Purified cosmid DNA is adjusted to a concentration of 200 ng/μl. A cosmid containing a reporter gene (EDH17B), detectable by a radioactive probe to this gene, is included. The biotinylation reaction is set up with the following including reagents from a Boehringer Mannheim nick translation kit: 10 μl cosmid contig [200ng/μl], 4 μl 10x buffer, 2 μl each dGTP, dATP, dTTP, dCTP, 0.2 μl of 1 μmM biotin-16-dUTP (Boehringer Manheim), 1 μl αdCTP $^{32}$P, 12.8 μl water and 4 μl enzyme. The reaction is incubated at 15° C. for 60–90 minutes, inactivated at 65° C. for 10 minutes, and passed through a G-50 Sephadex column.

100 μl Dynal streptavidin-coated magnetic beads (Dynel Inc., Lake Success, New York) are washed 3x in 100 μl binding buffer and resuspended in 100 μl of binding buffer. 1 μl of biotinylation reaction is added, mixed gently, and incubated for 15 min at room temperature, mixing occasionally. Beads are separated from solution using a magnetic particle concentrator. The beads and solution are counted separately. A bead:solution ratio of 5:1 or greater is desired; otherwise, the unbiotinylated cosmid DNA is purified further and re-biotinylated. The biotinylated cosmid clones are ethanol precipitated, washed in 70% ethanol, air dried, and resuspended in 20 μl water.

Primary selection is as follows: For blocking cDNA, the following ingredients are mixed in a 0.5 ml eppendorf tube; 8 μl pooled cDNA (or cDNA and water), 2 μl human COT-DNA [1 μg/μl] (Gibco BRL) and an overlay of mineral oil. This mixture is denatured at 95° C. for 5 min, 2x hybridization solution (1.5M NaCl, 40 mM sodium phosphate pH 7.2, 10 mM EDPA, 10X Denhardt's solution and 0.2% SDS) is prewarmed to 65° C. and 10 μl quickly added to the cDNA and mixed gently. This mixture is incubated at 65° C. for 4 hr.

Selection is carried out as follows: Five μl [200 ng] of pooled biotinylated cosmids are denatured in a 0.5 ml eppendorf tube overlayed with mineral oil. Blocked cDNA (20 μl) is added to the tube and mixed. 5 μl 2x hybridization solution is added and annealing occurs at 65° C. for 54–72 hr.

Elution of primary cDNA with magnetic beads is as follows: 150 μl Dynabeads M280 beads (DYNAL, Inc, Lake Success, N.Y.) are washed in 3x binding buffer and resuspended in 150 μl binding buffer. Primary selected cDNA is added to the beads, and the mixture is incubated at room temperature for 15 min with gentle mixing, washed 2x with 1 ml wash solution 1 for 15 min, washed 2x at 65° C. with 1 ml wash solution 2 for 15 min. Primary cDNA is eluted from the beads in 50 μl of 1M NaOH, 10 min and neutralized with 50 μl 1M Tris pH 7.5. The eluant is passed through a G-50 Sephadex column to collect primary cDNA.

Amplification of 1° cDNA and 2° selection is as follows: primary selected cDNA is amplified as described above, an aliquot applied to an agarose gel, blotted and the blot hybridized to the reporter gene. Amplified primary selected cDNA is carried through a secondary selection procedure (a repeat of primary selection) to produce secondary selected cDNA.

Cloning the 2° selected cDNA is as follows: secondary selected cDNA is amplified, purified, and restricted. The restricted 2° selected cDNA is ligated to restricted λgt10 as follows: 1 μl (100 ng) 2° cDNA, 1 μl 10× buffer, 6 μl H$_2$O, 1 μ-λgt10, CIAP arms (1 μg) (Stratagene, San Diego, Calif.), 1 μl T$_4$DNA ligase, at 15° C. overnight.

Packaging of ligation and plating of 2° selected material is as follows: the Stratagene protocol is followed (Stratagene, San Diego, Calif.) as described in the Gigapack® II Packaging Extract Kit. The packaged material is mixed with 30 μl C600 HflA cells at 37° C. for 20 min. 3 ml Tryptone broth top agar containing a final concentration of 10 mM MgSO$_4$ is added, mixed and poured onto LB Mg agar plates which are incubated at 37° C. overnight.

Analysis of 2° selected cDNA clones in as follow: from each of 96 phage plaques, 5 μl of phage lysate is amplified with λgt10 forward and reverse primers. An aliquot is applied to an agarose gel for sizing the inserts. Ten dot blots of each microtiter plate PCR™ product are made using 4.5 μl DNA per well (96 wells per microliter plate). Ten random inserts are selected, $^{32}$P probes were made and each hybridized to the dot blots and to a dot blot containing the cosmids used in the selection. This procedure localizes the insert and indicates overlapping cDNA clones. Clones of interest are sequenced using the Gibco BRL double stranded cycle sequencing kit by sequencing the amplified inserts. The PCR™ product is isopropanol precipitated prior to sequencing to eliminate excess λgt10 primers. If further sequence is needed, the inserts are subcloned into a plasmid or M13 vector to do standard Sanger sequencing using USB Sequenase® (United States Biochemical Corporation).

After two-rounds of hybridization/PCR™ amplification have been performed, selected cDNA inserts will be cloned into the recombinant bacteriophage, lambda gt10. In order to screen out non-specific cDNAs, plaque lifts from the selected library will be prepared (approximately 1,000 phage per large plate). Contaminating clones will be screened out on the basis of hybridization to total human genomic DNA, Bluescript® and mitochondrial DNA. Plaque lifts will also be hybridized with a reporter gene to determine the efficiency of the selection. A reporter can be a gene known to lie within a cosmid contig, or be a gene encoded by a cosmid that is not from the region, but where the cosmid encoding it is incorporated in the selection strategy.

PCR™ will then be performed on single cDNAs (after they have been checked for chimerism by cleavage with the enzyme used to generate the vector insertion site). These PCR™ amplified cDNA inserts will be dotted onto nylon filters in a microtiter plate format. Probes will then be generated individually from single cDNA inserts and hybridized to the cDNA insert and cosmid DNA dot blots. This identifies overlapping cDNAs, and maps the cDNAs back to cosmids.

Unique cDNAs will then be mapped back to Southerns containing genomic DNA, somatic cell hybrid DNA, DNA from pooled YACs from the region, and DNA from pooled cosmids from the region. DNA concentrations will be adjusted so that hybridization signals in each lane are similar.

Candidate cDNAs will then be sequenced directly with a modified cycle sequencing strategy and sequence comparisons with previously isolated genes are made with the "blast" and "fasta" programs.

The exon-trapping scheme described by A. Buckler and colleagues (Church et al. 1994) will be followed with the modified vector pSPL3. Exon-trapped clones will be sequenced and comparisons with HIV sequences will be performed to eliminate background clones. Expression patterns of apparently bona-fide clones will be determined, initially, by RT-PCR™ with primers for the ends of the exon. These primers will also be used on cosmids, YACs, and somatic-cell hybrids to confirm the genomic location of the sequence. Once a tissue in which the exon is expressed is identified, a cDNA library constructed from the same source will be screened with the trapped exon to identify a longer cDNA. A similar approach will be used to generate longer clones for selected cDNAs.

PCR™ of DNA from cDNA libraries will be performed with primers generated from cDNA sequences to determine expression profiles of genes. cDNA libraries from thymus, bone-marrow, fetal kidney, eye, macrophage, spleen, pancreas, fetal liver, lymphocyte, adult testes, tracheal epithelia, placenta, infant brain, and He-La cells may be examined. More conclusive expression patterns and sizes of RNAs will be determined on Northern blots.

EXAMPLE 11

Screen for Mutations in Candidate Genes in Linked Individuals

Genes will be screened on Northern blots derived from lymphoblastoid lines of patients, unaffected family members and normal controls. The present inventors obtain RNA from transformed keratinocytes of psoriasis patients and unaffected individuals. This will identify genes with altered expression patterns in psoriasis patients. Genes with altered expression patterns in psoriasis patients versus normal controls will be preferentially selected for mutational analysis.

Candidate genes will also be screened on Southern blots containing DNA of patients and unaffected individuals. High molecular weight DNA can be prepared in agarose plugs from transformed lines and used for pulsed-field gel analysis to look for large rearrangements in patients.

If no psoriasis specific alterations are detected, a more fine-structure analysis such as SSCP (Orita et al. 1989a; 1989b) or DNA sequencing will follow.

Genes will be screened for mutations in linked family members by RT-PCR™ followed by SSCP and then direct sequencing. The detection of a variant in patients will require sequencing of linked individuals and normal individuals to determine the molecular defect.

The inserts will be used to determine if the susceptibility locus exists in DNAs from members of high risk families, from linked-family members, and sporadic cases. This can be achieved most simply with Southern blotting and hybridization with a cDNA probe. Fairly large DNA rearrangements of greater than 500 bp may be detected in this manner. However, it may be that the mutations are too small to detect by Southern blotting. This would be the case if they are due to point mutations or to small insertions, deletions or other rearrangements.

One sure method of detecting mutations is by DNA sequencing. However, this can be a laborious task, particularly if the gene is very large. Sequencing can be performed on a genomic DNA template or a cDNA template prepared from RNA by reverse transcriptase. PCR™ allows one to sequence rapidly and directly from a complex template, but problems still remain. If one has identified a cDNA, one needs to obtain the corresponding cDNA species from RNA derived from members of linked families. The isolation of RNA, which is particularly labile, is not always easy; in addition, the gene may not be expressed in a tissue that is easily obtained.

In an attempt to detect mutations rapidly, several methods have been described; chemical cleavage (Cotton et al., 1988; Rodrigues et al., 1990), denaturing gradient electrophoresis (DGGE) and ribonuclease cleavage (Myers et al., 1988), and SSCP (single strand conformation polymorphism (a,b). None detect all mutations, but all have a relatively high success rate. All these methods are currently performed most successfully after PCR™ amplification of the region under study. Mutation scanning may be performed on cDNA derived from the appropriate tissue of psoriasis patients, or on genomic DNA. Even once it is possible to amplify all exons by PCR™, detection of mutations in genomic DNA may be hard if the location within the gene is variable.

Purification of DNA for sequencing is as follows: DNA is isolated and purified from blood or other DNA source such as a buccal swab or mouthwash from the individual to be screened using purification protocols known to one skilled in the art (Sambrook et al.). Blood samples are diluted with 2 volumes RBC lysis buffer (79 mg $NH_4HCO_3$, 6.1 g $NH_4Cl$, $H_2O$ to 1 liter, filter using a sterile filter (0.2 $\mu$), aliquot into 50 mL tubes and store at 4° C.) and held on ice for 30 minutes before DNA extraction. Purified DNA is adjusted to a concentration of about 100 ng/$\mu$l.

Amplification of exons is as follows: PCR™ exons to be sequenced are obtained using the following procedure: Approximately 100 ng of DNA is amplified in an appropriate volume (20 $\mu$l). Two sets of primers derived from the genomic sequence are used to amplify genomic DNA spanning at least 1 exon. Each reaction contains 0.5 $\mu$l (10 $\mu$M) of each primer, 3.2 $\mu$l dNTP [1.25 mM], 1.2 $\mu$l $MgCl_2$[25 mM], 2 $\mu$l BRL PCR™ buffer [10×], 0.1 $\mu$l BRL Taq polymerase and 0.05 $\mu$l spermidine [100 mM]. Generally, DNA is put in the tube and 19 $\mu$l of cocktail is added containing the above ingredients plus the correct amount of $H_2O$. One drop of Sigma H-5904 mineral oil is layered over the sample if not using a Perkin Elmer 9600. Amplification is as follows: 5 min at 95° C., 30 cycles of 30 s at 95° C., 30 s at 55° C., 1 min at 72° C., final 7 min at 72° C. extension. 5 $\mu$l of product is loaded on 1% agarose to verify that PCR™ reaction worked. The remaining 15 $\mu$l is used for sequencing.

Sequencing of PCR™ product is as follows: This procedure is an adaptation of the BRL double stranded cycle sequencing kit protocol. Isopropanol precipitate 15 $\mu$l PCR™ product by adding 15 $\mu$l $NH_4OAc$ and 30 $\mu$l isopropanol. Leave at room temperature for 12 minutes, spin at full speed in microfuge, 4° C. for 20 minutes, wash with 200 $\mu$l 70% EtOH, spin, 4° C., for 10 minutes, swab tube and air dry the pellet which may not be visible. Resuspend in 16 $\mu$l $H_2O$ and use 4 $\mu$l per sequencing reaction. Kinase primers as follows: 1 reaction for each sequencing reaction; 2 $\mu$l 0.4 $\mu$M primer, 1 $\mu$l 5X kinase buffer, 0.3 $\mu$l $\gamma$ATP $^{32}$P (NEN Dupont), 1 $\mu$l T4 polynucleotide kinase, 0.7 $\mu$l $H_2O$; incubate 37° C. for 10 minutes and heat to 55° C. for 5 minutes to stop reaction.

Sequencing reactions are as follows: aliquot 2 $\mu$l termination mixes into G, A, T, C tubes, compatible with PCR™ machine of choice; 4 tubes per sample, add 5 $\mu$l kinased primer to 5 $\mu$l of precipitated PCR™ product in microfuge tube, add 26 $\mu$l sequencing cocktail to 10 $\mu$l primer DNA mixture, mix, spin down. Sequencing Cocktail: 21.2 $\mu$l $H_2O$, 4.5 $\mu$l 10× sequencing buffer, 0.3 $\mu$l Taq DNA polymerase. Aliquot 8 $\mu$l of sequence mixture into termination tubes containing termination mix. Make sure all 10 $\mu$l of liquid is in bottom of tubes, if not, spin down. Amplify as follows: 5 min at 95° C., 20 cycles 30 s at 95° C., 30 s at 55° C., 1 min at 70° C., 10 cycles 30 s 95° C., 30 s at 55° C. Add 5 $\mu$l STOP solution immediately when cycling is complete. Load on 6.5% polyacrylamide—urea gel, heat samples to 95° C. 5' before loading, load 2–3 $\mu$l per well, and expose to film overnight or less time if necessary.

If there are a series of mutations, it may be possible to amplify altered exons with PCR™, dot blot the reaction products onto nylon membrane, and hybridize with a series of oligonucleotide probes, as is performed for the detection of HLA alleles.

If RNA can be prepared from an accessible source, such as blood, the RNA would be isolated. cDNA would be made with reverse transcriptase (RT-PCR™ kits can be used). The gene could then be sequenced by the protocol described above, with oligonucleotide primers derived from the cDNA sequence.

Population screens may be performed using antibody screening. The present invention contemplates an antibody that is immunoreactive with a polypeptide encoded by wild-type or by a mutant ILF or IL nucleic acid sequence. An antibody may be a polyclonal or a monoclonal antibody. In a preferred embodiment, an antibody is a monoclonal antibody. Means for preparing and characterizing antibodies are well known in the art (See, e.g., Antibodies "A Laboratory Manual, E. Howell and D. Lane, Cold Spring Harbor Laboratory, 1988).

Antibodies, both polyclonal and monoclonal, specific for a polypeptide encoded by a wild-type or mutant ILF or IL gene of the present invention may be prepared using conventional immunization techniques, as will be generally known to those of skill in the art. A composition containing antigenic epitopes of said polypeptide may be used to immunize one or more experimental animals, such as a rabbit or mouse, which will then proceed to produce specific antibodies against the polypeptide. Polyclonal antisera may be obtained, after allowing time for antibody generation, simply by bleeding the animal and preparing serum samples from the whole blood.

To obtain monoclonal antibodies, one would also initially immunize an experimental animal, often preferably a mouse, with a polypeptide composition encoded by wild-type or mutant ILF or IL. One would then, after a period of time sufficient to allow antibody generation, obtain a population of spleen or lymph cells from the animal. The spleen or lymph cells are then fused with cell lines, such as human or mouse myeloma strains, to produce antibody-secreting hybridomas. These hybridomas may be isolated to obtain individual clones which are then screened for production of antibody to the desired polypeptide.

EXAMPLE 12

Gene Therapy

This prophetic example describes some of the ways in which the present invention may be of use in the treatment of early onset psoriasis via gene therapy. A wild-type psoriasis gene may be introduced into human tissue to provide a wild-type copy of the gene and therefore, also a wild-type protein product, that may correct the genetic lesion that causes the familial form of psoriasis.

Human adenoviruses or retrovirus are means for introducing genes into tissue. Adenoviruses are double-stranded DNA tumor viruses with genome sizes of approximate 36 kb. As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

In general, adenovirus gene transfer systems are based upon recombinant, engineered adenovirus which is rendered replication incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 kb of foreign DNA and can be grown to high titers. Persistent expression of transgenes follows adenoviral infection.

Particular advantages of an adenovirus system for delivering foreign genes and their protein products to a cell include (i) the ability to substitute relatively large pieces of viral DNA with foreign DNA; (ii) the structural stability of recombinant adenoviruses; (iii) the safety of adenoviral administration to humans; (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible.

Human subjects testing positive for a familial psoriasis susceptibility locus and for whom the medical indication for adenovirus-mediated gene transfer has been established would be tested for the presence of antibodies directed against adenovirus. If antibodies are present and the patient has a history of allergy to either pharmacological or naturally occurring substances, application of a test dose of on the order of $10^3$ to $10^6$ recombinant adenovirus under close clinical observation would be indicated.

Recombinant adenovirus providing the wild-type ILF or IL gene is prepared and purified by any method that would be acceptable to the Food and Drug Administration for administration to human subjects, including, but not limited to cesium chloride density gradient centrifugation, and subsequently tested for efficacy and purity. Virus is administered to patients by means of intravenous administration in any pharmacologically acceptable solution, either as a bolus or as an infusion over a period of time. Generally speaking, it is believed that the effective number of functional virus particles to be administered would range from $5 \times 10^{10}$ to $5 \times 10^{12}$.

Patients would remain hospitalized for at least 48 hr to monitor acute and delayed adverse reactions. Serum levels of a protein product may be monitored or Southern blots may be performed to follow the efficacy of the gene transfer. Adjustments to the treatment may include adenovirus constructs that use different promoters or a change in the number of pfu injected.

If genes are not expressed in lymphoblastoid lines, PCR™ systems for amplifying the genes from genomic DNA will be developed.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Albertsen, et al. *Proc. Nat'l. Acad. Sci. USA*, 87:4256–4260, 1990.
Baadsgaard et al., *J. Invest. Dermatol.*, 95:328 (1990).
Baker et al., *Br. J. Dermatol.*, 126:493 (1993).
Barker, *Lancet*, 338:227 (1991).
Beckmann et al., *Hum. Molec. Genet.*, 2:2019 (1993).
Bell et al., *Diabetes*, 33:176 (1984).
Bos, *Br. J. Dermatol.*, 118:141 (1988).
Bowcock et al., *Genomics*, 15:376 (1993).
Brandrup et al., *Arch. Dermatol.*, 114:874 (1978).
Brownstein et al. *Science*, 244:1348–1351, 1989.
Christophers and Henseler, *Acta Dermato-Venereol. Suppl.*, 151:88 (1989).
Chumakov et al. *Nature*, 359:380–387, 1992.
Church, et al., *Nature Genet.*, 6:98–105.
Civatte et al., *Ann. Dermatol. Venereol.*, 104:525 (1977).
Cotton et al., *Proc. Natl. Acad. Sci. USA*, 85:4397–4401 (1988).
Duvic, J. *Invest Dermatol.*, 95:385 (1990).
Duyk et al., *Proc. Natl. Acad. Sci. U.S.A.*, 87:8995 (1990).
Espinoza et al., *J. Rheumatol.*, 7:445 (1980).
Feder et al., *Am. J. Hum. Genet.*, 37:635 (1965).
Fernandez-Vina et al., *Hum. Immunol.*, 30:60 (1991a).
Fernandez-Vina et al., *Immunogenetics*, 34:299 (1991b).
Green and Olson *Proc. Natl. Acad. Sci. USA*, 87:1213–1217, 1990.
Hall et al., *Science*, 250:1684 (1990).
Henseler and Christophers, *J. Am. Acad. Dermatol.*, 13:450 (1985).
Jelinek *Proc. Natl. Acad. Sci. USA*, 77:1398–1402, 1980.
Julier et al., *Nature*, 354:155 (1991).
Karvonen et al., *Ann. Clin. Res.*, 8:298 (1976).
Kyte & Doolittle, *J. Mol. Biol.*, 157:105–132 (1982).
Lander and Green, *Proc. Natl. Acad. Sci. U.S.A.*, 84, 2363 (1987).
Lathe, R., *J. Mol. Biol.*, 183:1–12,4 (1985).
Lathrop et al., *Proc. Natl. Acad. Sci. U.S.A.*, 81:3443 (1984).
Ledbetter et al., *Genomics*, 6:475–481 (1990).
Li et al., *Proc. Natl Acad. Sci. U.S.A.*, 88:7739 (1991).
Li et al., *Genomics*, 13:665 (1992).
Lovett, et al., *Proc. Natl. Acad. Sci. U.S.A.*, 88:9628 (1991).
Malice et al., *Nature Genet.*, 6:384 (1994).
Menter and Barker, *Lancet*, 338:231 (1991).
Morgan et al., *Nucleic Acids Res.*, 20:5173–5179 (1992).
Mukaida et al., *J. of Immunology*, 143(4):1366–1371 (1989).

Myers et al., In: Davies, K. (ed.) *Genome Analysis: A Practical Approach*, IRL Press, 95–130 (1988).
Nelson, D. *Proc. Nat'l. Acad. Sci. USA*, 86:6686–6690, 1989.
Orita, et al., *Proc. Natl. Acad. Sci., U.S.A.*, 86:2766–2770 (1989a).
Orita, et al., *Genomics*, 5:874–879 (1989b).
Ott, *Analysis of Human Genetic Linkage*, (Johns Hopkins University Press, Baltimore, Md., 1991).
Parimoo et al., *Proc. Natl. Acad. Sci. U.S.A.*, 88:9623 (1991).
Pietrzyk et al., *Arch. Dermatol. Res.*, 273:295 (1982).
Riley, et al. (1990).
Rodrigues et al., *Proc. Natl. Acad. Sci. USA*, 87:7555–7559 (1990).
Rosenthal, et al., *Nucl. Acids Res.*, 18:3095–3096 (1990).
Sambrook et al., Molecular cloning: A laboratory manual. Cold Spring Harbor Laboratory. Cold Spring Harbor, N.Y. (1989).
Spielman et al., *Am. J. Hum. Genet.*, 52:506 (1993).
Sucider et al., *Proc. Natl. Acad. Sci. U.S.A.*, 88:4005 (1991).
Talkainen et al., *Br. J. Dermatol.*, 192:179 (1980).
Thomson et al., *Genet. Epidemiol.*, 8:155 (1989).
U.S. Pat. No. 4,554,101
U.S. Pat. No. 4,603,102
Watson et al., *Arch. Dermatol.*, 105:197 (1972).
Weeks and Lange, *Am. J. Hum. Genet.*, 50:859 (1992).
Weeks and Lange, *Am. J. Hum. Genet.*, 42:316 (1988).
Weissenbach et al., *Nature*, 859:794 (1992).

What is claimed is:

1. A method for screening for psoriasis susceptibility comprising:
   (a) obtaining a nucleic acid sample from a patient suspected of having susceptibility to psoriasis; and
   (b) determining whether a polymorphic marker associated with a familial psoriasis susceptibility locus is present; wherein said polymorphic marker is linked with a gene for interleukin enhancer binding factor.

2. The method of claim 1 wherein the sample is screened with a probe comprising a sequence that hybridizes to a distal region of human chromosome 17q.

3. The method of claim 1, wherein the sample is screened with a probe comprising an intron sequence of human chromosome 17q, said intron sequence further defined as located distal to genetic marker D17S784 of human chromosome, 17q and within a gene encoding for interleukin enhancer binding factor.

4. The method of claim 1, wherein tee sample is screened with a probe comprising the nucleotide sequence as set forth in any one of SEQ ID NOS:4–6, or a sequence complementary to said nucleotide sequence.

5. The method of claim 1, wherein the sample is screened with a nucleic acid molecule comprising the nucleotide sequence as set forth in SEQ ID NO:6, or a fragment of said nucleotide sequence of from 15 to 100 nucleotides.

6. The method of claim 1 wherein the polymorphic marker is distal to genetic marker D17S784 of human chromosome 17q.

7. The method of clam 1 wherein the sample is screened with a probe having a sequence complementary to a region 5' of an intron containing a PstI or PvuII polymorphism within the gene for interleukin enhancer binding factor, or a probe having a sequence complementary to a region 3' to the intron, said probe having a length of between 18 bp and 1 million bp.

8. The method of claim 7 wherein the probe has a length of between 400 bp and 2,000 bp.

9. The method of claim 8 wherein the probe has a length of 450 bp.

10. The method of claim 8 wherein the probe is further defined as comprising the nucleotide sequence as set forth in SEQ ID NO:6, or its complement.

11. The method of claim 7 wherein the probe is further defined as comprising the nucleotide sequence as set forth in SEQ ID NO:4 or SEQ ID NO:5.

12. The method of claim 7 wherein the probe is further defined as comprising a nucleotide sequence that is complementary to the sequence as set forth in SEQ ID NO:4, or complementary to the sequence as set forth in SEQ ID NO:5.

13. The method of claim 1 wherein the polymorphic marker is linked to an intron of the interleukin enhancer binding factor gene.

14. The method of claim 13 wherein the polymorphic marker is further defined as a PvuII polymorphism.

15. The method of claim 13 wherein the polymorphic mark is further defined as a PstI polymorphism.

16. The method of claim 1, wherein the sample is screened with a probe for detecting a polymorphic marker associated with a familial psoriasis susceptibility locus in families with a psoriasis afflicted member, said probe having a DNA sequence mapping within about 11 cM region distal to a genetic marker D17S754 of human chromosome 17q, said probe prepared by a process comprising the steps of:
   (a) obtaining yeast artificial chromosomes containing human sequences from chromosome 17q between markers D17S784 and D17S928;
   (b) obtaining a cosmid library containing human sequences from chromosome 17q;
   (c) selecting cosmids having sequences represented in the yeast artificial chromosome library;
   (d) obtaining tissue specific primary cDNAs;
   (e) selecting a cDNA from the primary cDNAs having sequences represented in the selected cosmids; and
   (f) screening the selected cDNA for sequences that map to human chromosome 17q
wherein said DNA of said probe is a sequence that maps and hybridizes to a region distal to genetic marker D17S784 of human chromosome 17q.

17. The method of claim 16 wherein the hybridization of the DNA sequence to a human DNA sequence detects a sequence altered from a wild-type sequence in a sample DNA from a patient with a familial form of psoriasis.

18. The method of claim 16 wherein the step of obtaining yeast artificial chromosomes includes the steps of:
   (a) annealing sequences of DNA having between 15 to 40 nucleotides from a region of human chromosome 17 distal to genetic marker D17S784 with a human chromosome 17 YAC library; and
   (b) selecting the human chromosome YACs that bind the sequences.

19. The method of claim 16 wherein the selecting cosmids step includes the steps of:
   (a) obtaining probes from the yeast artificial chromosomes using inverse repeated sequence polymerase chain reaction probes;
   (b) annealing the probes with human DNA having repetitive sequence;
   (c) incubating the annealed probes with the cosmid library; and
   (d) selecting cosmids which bind the annealed probes.

20. The method of claim 16 wherein the tissue-specific primary cDNA are obtained from epithelial cells, activated T-cells, or keratinocytes.

21. The method of claim 16 wherein the selecting a cDNA step includes the steps of:
   (a) adding linkers to the primary cDNAs to form linkered cDNA;
   (b) amplifying the linkered cDNA;
   (c) labeling the cosmids to form labeled cosmids;
   (d) hybridizing labeled cosmids to the linkered cDNA; and (e) isolating linkered cDNA that hybridizes to the labeled cosmids.

22. The method of claim 16 wherein the screening step further comprises hybridizing the selected cDNA to DNA samples from psoriasis affected members in genetically linked psoriasis families.

23. The method of claim 16 wherein the screening step further comprises sequencing the selected cDNA and corresponding DNA from affected members in psoriasis linked-families.

24. A method for detecting a genetic polymorphism associated with familial psoriasis in a chromosome 17q distal region comprising:
   (a) identifying a patient suspected of having a susceptibility for developing psoriasis;
   (b) preparing a probe that includes a sequence that hybridizes to a polymorphic region at the distal end of human chromosome 17q;
   (c) contacting a DNA sample isolated from a human tissue of the patient with the probe for a sufficient amount of time to allow for the specific hybridization of the sample DNA to the probe under stringent hybridization conditions; and
   (d) determining the presence of specific hybridization between the sample DNA and the probe;
wherein the presence of specific hybridization of the probe and the sample DNA provides for the detection of a genetic polymorphism associated with familial psoriasis susceptibility at the distal end of human chromosome 17q.

25. The method of claim 24, wherein the probe hybridizes with a polymorphic marker linked with a gene for interleukin enhancer binding factor.

26. The method of claim 25, wherein the probe hybridizes with a polymorphic marker defined by an intron of the gene for interleukin enhancer binding factor.

27. A DNA probe comprising a polymorphism located within an intron region of the gene encoding for interleukin enhancer binding factor, said intron region being located within a region of the interleukin binding factor gene sequence flanked by the nucleic acid sequences as set forth in SEQ ID NO:4 and SEQ ID NO:5.

28. A method for identifying a nucleic acid sequence for screening for familial psoriasis susceptibility comprising:
   (a) obtaining a nucleic acid sample from a patient having psoriasis or suspected of having susceptibility to psoriasis;
   (b) identifying a family specific allele comprising a polymorphic marker associated with a familial psoriasis susceptibility locus, wherein the polymorphic marker is present in the patient's nucleic acid sample and is not present in a control nucleic acid sample, and wherein the polymorphic marker maps to chromosome 4 between 4q13 and 4q21; and
   (c) identifying a nucleic acid sequence that can be used to detect the polymorphic marker;
thereby identifying a nucleic acid sequence for screening for familial psoriasis susceptibility.

29. The method of claim 28 wherein the polymorphic marker has a recombination factor with genetic marker D4S400 of about 0.036 and an lod score of about 4.

30. The method of claim 28 wherein the polymorphic marker is linked with a gene for interleukin 8.

31. The method of claim 28, wherein the nucleic acid sequence comprises the nucleotide sequence as set fort in any one of SEQ ID NOS:7–16.

32. An isolated DNA segment of from 20 to 100 nucleotides in length and comprising the nucleic acid sequence as set forth in any one of SEQ ID NOS:7–16, or a sequence complementary to said nucleic acid sequence.

* * * * *

UNITED STATES PATENT AND TRADEMARK OFFICE
CERTIFICATE OF CORRECTION

PATENT NO. : 5,811,233

DATED : September 22, 1998

INVENTOR(S) : Bowcock et al.

It is certified that error appears in the above-identified patent and that said Letters Patent is hereby corrected as shown below:

Title page, item [57], line 9, after 'within', insert --or--.
In claim 4, column 37, line 29, delete "tee" and insert --the-- therefor.
In claim 15, column 37, line 67, delete "mark" and insert --marker-- therefor.
In claim 16, column 38, line 16, delete "D17S754" and insert --D17S784-- therefor.
In claim 20, column 38, line 58, delete "cDNA" and insert --cDNAs-- therefor.
In claim 24, column 39, line 12, after 'psoriasis' insert --susceptibility--.
In claim 31, column 40, line 29, delete "fort" and insert --forth-- therefor.

Signed and Sealed this

Twelfth Day of January, 1999

Attest:

*Attesting Officer*     *Acting Commissioner of Patents and Trademarks*